US011978557B2

(12) United States Patent
Takemoto et al.

(10) Patent No.: US 11,978,557 B2
(45) Date of Patent: May 7, 2024

(54) DIAGNOSIS SUPPORT SYSTEM AND METHOD

(71) Applicant: Splink, Inc., Tokyo (JP)

(72) Inventors: Kempei Takemoto, Tokyo (JP); Wataru Kasai, Tokyo (JP); Yuki Aoyama, Tokyo (JP)

(73) Assignee: Splink, Inc., Tokyo (JP)

( * ) Notice: Subject to any disclaimer, the term of this patent is extended or adjusted under 35 U.S.C. 154(b) by 718 days.

(21) Appl. No.: 16/973,708

(22) PCT Filed: Sep. 12, 2019

(86) PCT No.: PCT/JP2019/035914
§ 371 (c)(1),
(2) Date: Dec. 9, 2020

(87) PCT Pub. No.: WO2020/054803
PCT Pub. Date: Mar. 19, 2020

(65) Prior Publication Data
US 2021/0257094 A1    Aug. 19, 2021

(30) Foreign Application Priority Data

Sep. 12, 2018    (JP) .................................. 2018-170708
Mar. 29, 2019    (JP) .................................. 2019-067854

(51) Int. Cl.
*G16H 50/20*    (2018.01)
*A61B 6/00*    (2006.01)
(Continued)

(52) U.S. Cl.
CPC ........... *G16H 50/20* (2018.01); *A61B 6/5235* (2013.01); *A61B 6/5247* (2013.01); *G16H 30/40* (2018.01);
(Continued)

(58) Field of Classification Search
CPC ........ G16H 30/20; G16H 30/40; G16H 50/20; G16H 10/40; G16H 40/40; G16H 50/50
(Continued)

(56) References Cited

U.S. PATENT DOCUMENTS 10,438,380 B2    10/2019 Hu et al.
2004/0028389 A1*    2/2004 Naohara ............... G11B 27/002
(Continued)

FOREIGN PATENT DOCUMENTS

JP    2006/320387 A    11/2006
JP    2017/058287 A    3/2017
(Continued)

OTHER PUBLICATIONS

Extended European Search Report for EP19859252.9, dated Apr. 29, 2022, 8 pgs.
(Continued)

*Primary Examiner* — Ajibola A Akinyemi
(74) *Attorney, Agent, or Firm* — Blank Rome LLP

(57) ABSTRACT

A system (10) that provides diagnosis support information (110) relating to a disease of a target subject (5) includes: an acquisition unit (11) that acquires subject information (105) including actual image data (15) of an MR image including at least a reference region including part of an evaluation target region of the subject; and an information providing unit (12) that provides diagnosis support information (110) based on pseudo PET image data (115) of the evaluation target region generated by an image processing model (60) machine learned with training data (70) including actual image data (71) of a MR image of a reference region and actual image data (72) of a PET image including the evaluation target region of a plurality of test subjects so as to generate pseudo PET image data (75) of the evaluation target region from actual image data (71) of an MR image
(Continued)

of the reference region, from the actual image data (15) of an individual MR image of the target subject.

30 Claims, 18 Drawing Sheets

(51) Int. Cl.
  *G16H 30/40* (2018.01)
  *A61B 5/055* (2006.01)
  *A61B 6/03* (2006.01)
(52) U.S. Cl.
  CPC .............. *A61B 5/055* (2013.01); *A61B 6/032* (2013.01); *A61B 6/037* (2013.01)
(58) Field of Classification Search
  USPC ........................................................ 382/128
  See application file for complete search history.

(56) References Cited

U.S. PATENT DOCUMENTS

| | | | |
|---|---|---|---|
| 2006/0133564 A1* | 6/2006 | Langan | ............... A61B 6/5258 378/8 |
| 2017/0372497 A1 | 12/2017 | Hu et al. | |

FOREIGN PATENT DOCUMENTS

| | | |
|---|---|---|
| JP | 2018/505705 A | 3/2018 |
| KR | 2018/0097214 A | 8/2018 |
| WO | WO-2018/048507 A1 | 3/2018 |

OTHER PUBLICATIONS

Tien-Duong Vu, et al., "Non-White Matter Tissue Extraction and Deep Convolutional Neural Network for Alzheimer's Disease Detection", soft Computing, https://doi.org/10.1007/s00500-018-3421-5, 2018, pp. 6825-6833.

M. Rahim, et al., "Transmodal Learning of Functional Networks for Alzheimer's Disease Prediction", IEEE Journal of Selected Topics in Signal Processing, vol. 10, No. 7, Oct. 2016, pp. 1204-1213.

International Search Report for PCT/JP2019/035914 dated Dec. 10, 2019, 4 pages.

"Deep Learning Concepts Understood from Optimization", Apr. 2015, pp. 191-197.

A. Sikka, et al., "MRI to FDG-PET: Cross-Modal Synthesis Using 3D U-Net for Multi-Modal Alzheimer's Classification", https://arxiv.org/abs/1807.10111v1, Jul. 26, 2018, 10 pgs.

* cited by examiner

DIAGNOSIS SUPPORT SYSTEM AND METHOD

RELATED APPLICATIONS

This application is a national phase of PCT/JP2019/035914, filed on Sep. 12, 2019, which claims the benefit of Japanese Application No. 2018-170708, filed on Sep. 12, 2018 and Japanese Patent Application No. 2019-067854, filed on Mar. 29, 2019. The entire contents of these applications are hereby incorporated by reference.

TECHNICAL FIELD

The present invention relates to a system and method that support diagnosis of a complex system, such as a living body.

BACKGROUND ART

A variety of tomography apparatuses (or "modalities"), such as CT (Computed Tomography), MRI (Magnetic Resonance Imaging), PET (Positron Emission Tomography), SPECT (Single Photon Emission Computed Tomography), and PET-CT are known as devices for diagnosing the morphologies and functions of test subjects (persons being tested, examinees, target subjects), and are used for diagnosing diseases such as dementia and Parkinson's disease. With PET and SPECT, images are generated by administering a radioactive medicine (medical agent) into the subject's body, such as by intravenous injection, and imaging with the radiation emitted from the medicine present in the body. From images with a medicine, it is possible for doctors to grasp not only the morphology of each part inside the body but also how the medicine administered into the body is distributed and how substances in the body that react with the medicine have accumulated, which can contribute to higher accuracy in diagnosing diseases. As one example, PET images that are obtained using a substance called "Pittsburgh compound B" as a PET radiopharmaceutical (tracer), are useful for differential diagnosis and/or early diagnosis of Alzheimer's-type dementia because the extent of accumulation of amyloid β protein in the brain is measured based on captured PET images.

Although images, such as PET images, obtained using medicines or drugs have various advantages, there are also a number of disadvantages. As one example, taking images using medicines is generally more expensive than imaging methods like MRI that do not use medicines. This can place a larger financial burden on the test subject or a health insurance organization that covers the examination cost for the test subject. In addition, when obtaining a PET image or the like using a radioactive medicine, a radioactive substance must be ingested into the body, even in a small amount, which carries a risk of exposure. There is a further problem in that to avoid adverse side effects, imaging using medicines cannot be performed on people suffering from specific diseases, such as kidney disease.

"MRI to FDG-PET: Cross-Modal Synthesis Using 3D U-Net For Multi-Modal Alzheimer's Classification" by Apoorva Sikka et al. on 30 Jul. 2018 (online, Cornell University Library, retrieved on 31 Aug. 2018 from the URL https://arxiv.org/abs/1807.10111v1, hereinafter referred to as "Sikka et al."), suggests that the diagnostic accuracy for Alzheimer's disease can be improved through analysis that combines magnetic resonance imaging (MRI), which measures brain atrophy, and positron emission tomography (PET), which quantifies hypometabolism, but also points out that this method is limited by the availability of scans corresponding to the respective modalities. For this reason, research focusing on a cross-modal approach that uses a 3D U-Net architecture to estimate FDG-PET scans from specific MR scans has also been disclosed. That publication states that the use of complete MR images instead of a local patch-based approach is useful in capturing non-local and non-linear correlations between the MRI and PET modalities. Note that the expression "FDG-PET image" refers to a PET image obtained by administering a medicine in which a "positron nuclide (that is, positron emitting nuclide)" is synthesized as a marker to glucose (dextrose).

Summary of Invention

Estimating images normally obtained with medicines, such as PET images, from images, such as MRI images, obtained without using medicines and using the estimated images for diagnosis reduces the burden placed on the subject and improves the accuracy of image-based diagnosis. For this reason, there is demand for supplying a system and/or a method that can improve the usefulness in estimated images and/or the information obtained from estimated images.

One aspect of the present invention is a system, for example, a diagnosis support system (diagnosis assistance system), including an acquisition unit that acquires individual actual first type image data (individual actual Type-1 image data) that includes at least a reference region, which includes an evaluation target region as a part, of a target subject. The system further includes an information providing unit that provides diagnosis support information (diagnosis assistance information) based on a set of pseudo second type image data (pseudo Type-2 image data) of the evaluation target region generated from the set of the individual actual first type image data (the individual actual Type-1 image data) of the target subject by an image processing model machine learned with training data that includes sets of actual first type image data (actual Type-1 image data) of reference regions of a plurality of test subjects and sets of actual second type image data (actual Type-2 image data) including evaluation target regions of the plurality of test subjects, so as to generate a set of the pseudo second type image data (pseudo Type-2 image data) of the evaluation target region from a set of the actual first type image data (actual Type-1 image data) of the reference region.

The image processing model is a machine leaned model (a model built by machine learning) based on training data (teacher data or learning data) including actual first type image data of a reference region, part of which is an evaluation target region, and actual second type image data which includes the evaluation target region, so as to generate pseudo second type image data of the evaluation target region from actual first type image data of the reference region. Unlike a different machine learned model to generate, from actual first type image data of a reference region, which includes the evaluation target region as a part, pseudo second type image data of the reference region, which is the same as that of the first type image data and part of which is the evaluation target region, the machine leaned image processing model according to the present invention generates pseudo second type image data that is limited to the evaluation target region. That is, the machine learned image processing model of this invention is a model that has been machine learned (trained) so as to generate pseudo second type image data of the evaluation target region by actively using information in the actual first type image data aside from the evaluation target region of the reference region. Accordingly, by using this image processing model, it is possible to generate pseudo second type image data of the evaluation target region with higher accuracy from the individual actual first type image data of the target subject and possible to provide diagnosis support information based on the pseudo image data.

The diagnosis support information provided from this system may include pseudo second type image data of the evaluation target region, may include individual actual first type image data, and may include a result of analyzing the pseudo second type image data and/or actual second type image data.

Description of Embodiments

Figure 1:
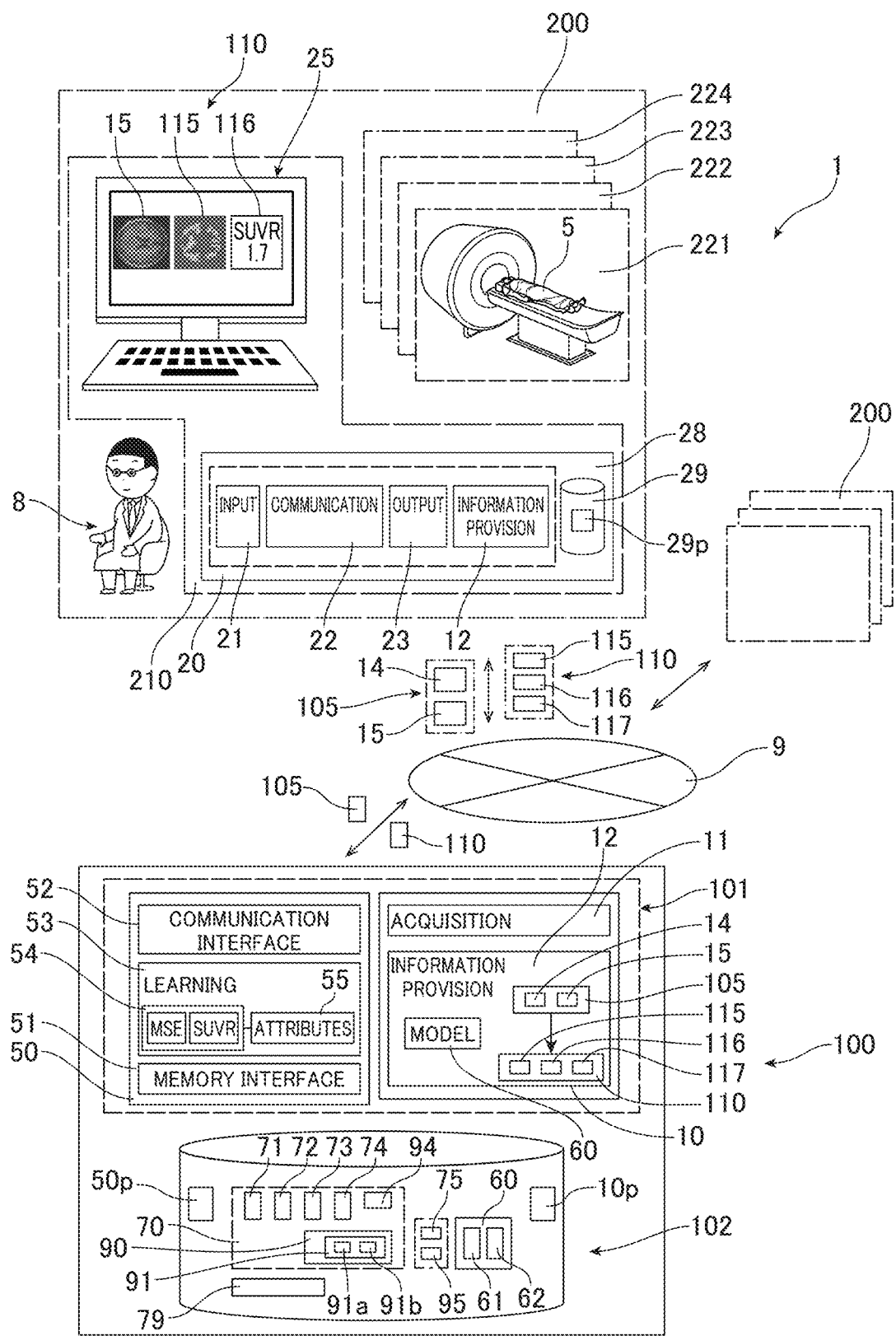
FIG. 1 is a diagram depicting one example of a diagnosis support network including a diagnosis support system.

FIG. 1 depicts an overview of a diagnosis support network including a diagnosis support system. The diagnosis support network (diagnosis assistance network) 1 includes terminals 210, which are installed at one or a plurality of medical institutions 200, and a diagnosis support system (diagnosis assistance system) 100 that is connected via the Internet (or cloud) 9 to the terminals 210 so as to communicate with the terminals 210. The medical institution 200 has tomography apparatuses (modalities) 221 to 224 that acquire images for diagnosing the morphology (form), functions, and the like of the subject (target subject, subject of the examination, patient) 5. One example of an imaging apparatus is the MRI apparatus 221 that acquires an MR image (MRI) 15 of the subject (patient) 5. Other examples may include the PET apparatus 222 that acquires PET images, the SPECT apparatus 223 that acquires SPECT images, and the CT apparatus 224 that acquires CT images. Each medical institution 200 does not need to be equipped with all of the tomography apparatuses 221 to 224, and the diagnosis support system 100 provides diagnosis support information 110 by estimating PET images or SPECT images based on the images acquired by the MRI apparatus 221 or the CT apparatus 224.

The terminal (diagnosis support terminal or medical assistance system) 210 of the medical institution 200 includes an image display apparatus 25, which provides the diagnosis support information (diagnosis assistance information) 110 to a doctor 8 or a medical technician, and a processing terminal 20. The processing terminal 20 is a computer terminal equipped with computer resources including a CPU 28 and a memory (storage medium) 29, and includes an input interface (acquisition interface, acquisition unit, acquisition function, or acquisition module) 21 that acquires attribute information 14 of the patient 5, a transmission/reception interface (communication interface, communication function or communication module) 22 that transmits subject information (patient information, recipient information) 105, which includes an MR image 15 taken by the MRI apparatus 221 and the attribute information 14 of the patient 5, to the diagnosis support system 100, and an output interface (output unit, output function, or output module) 23 that displays (outputs) the diagnosis support information 110 provided by the diagnosis support system 100 via the image display apparatus 25 or the like. The processing terminal 20 includes a program (program product) 29p which is downloaded and executed by the CPU 28 and includes instructions for executing the functions described above, This program 29p may be stored in the memory 29 or may be provided by an external recording medium.

The diagnosis support system 100, which provides the diagnosis support information 110 via the network 9 to the terminal 210 of the medical institution 200, includes a diagnosis support module (diagnosis assistance, diagnosis support function or diagnosis support unit) 10 and a model providing module (model provider, model providing function or model providing unit) 50. One example of the diagnosis support system 100 is a server equipped with computer resources including a CPU 101 and a memory (storage medium or first storage unit) 102. The diagnosis support system 100 includes programs (program products) 10p and 50p that are downloaded and executed by the CPU 101 and include instructions which execute functions as the modules 10 and 50 described above. The programs 10p and 50p may be stored in the memory 102 or may be provided by an external recording medium.

The diagnosis support module 10 includes an acquisition unit (acquisition interface, acquisition module or input interface) 11 that acquires the subject information (patient information) 105 including individual actual first type image data (individual actual Type-1 image data, individual real Type-1 image data) 15 (which includes at least a reference region covering part of an evaluation target region) including at least a reference region, which includes an evaluation target region as a part, of the target subject (patient) 5 and an information providing unit (information provision unit, information providing interface, information providing module, information providing function, or information output interface) 12 that provides the diagnosis support information (diagnosis assistance information) 110 obtained by a machine learned image processing model 60 from the patient information 105. The model providing module (model providing device) 50 that provides the image processing model 60 includes a memory interface 51 that can access the memory (storage or storage unit) 102 that stores training data (learning data or teaching data) 70, a learning unit (learning device, learning module or learning function) 53 that trains the image processing model 60 based on the training data 70, and a model output unit 52 that outputs the machine learned model (image processing model) 60.

The training data 70 includes sets of actual first type image data (actual Type-1 image data, real Type-1 image data) 71 of reference regions of a plurality of test subjects (examinees) and sets of actual second type image data (actual Type-2 image data, real Type-2 image data) 72 including evaluation target regions (regions to be evaluated, ROIs) for the respective test subjects. The "image data" referred to here is three-dimensional image data, which also applies to the following description. Based on the training data 70, the learning unit 53 provides the image processing model 60 that has undergone machine learning to learn how to generate a set of pseudo second type image data (pseudo Type-2 image data, estimated image data) 75 of the evaluation target region from a set of actual first type image data (actual Type-1 image data) 71 of a reference region. The information providing unit 12 of the diagnosis support module 10 provides the diagnosis support information 110 based on the pseudo Type-2 image data (estimated image data) 115 for the evaluation target region, which was generated by the image processing model 60 from individual actual Type-1 image data 15 for the target subject (patient) 5 included in the patient information 105.

Figure 2:
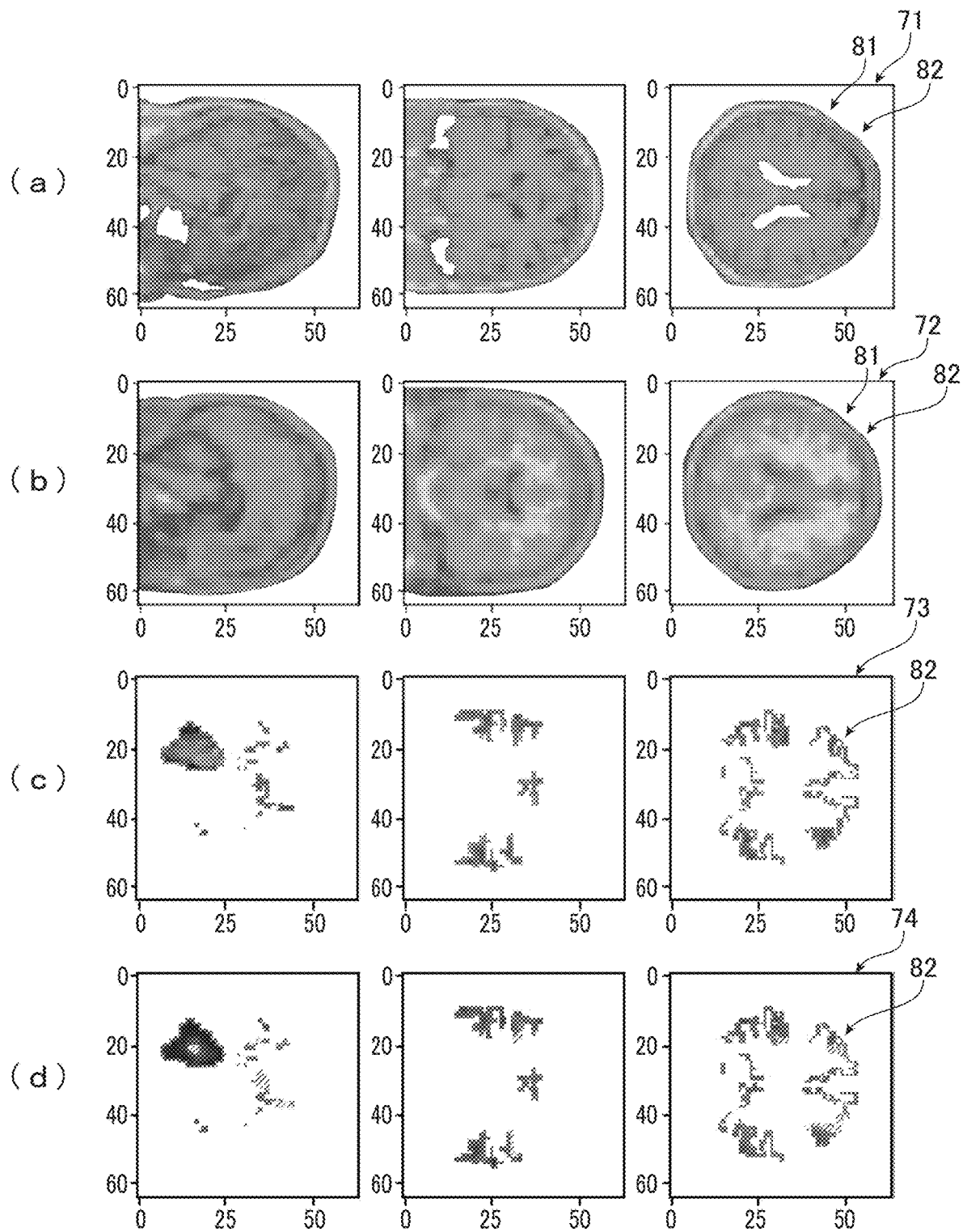
FIG. 2 is a diagram depicting an overview of training data, where row (a) is MR images of the entire brain, row (b) is PET images of the entire brain, row (c) is MR images of a region of interest (ROI, evaluation target region) in the brain, and row (d) is PET images of the region of interest of the brain.

FIG. 2 depicts a number of examples of images included in the training data 70. The images in the top level (Row (a)) are examples of a set of the actual Type-1 image data 71 of a reference region. The actual Type-1 image data 71 in the present embodiment is MR images (MRI) that make it possible to accurately acquire information focusing on the internal morphology of a living body, and is actual image data including a region 81 covering the entire brain as the reference region. Row (a) depicts the three-dimensional actual image data 71 by way of representative cross-sectional views at three locations. This also applies to the following description.

The images on the next level (Row (b)) are examples of a set of actual Type-2 image data 72 including an evaluation target region. The actual Type-2 image data 72 in the present embodiment, which has been captured using a medicine, is PET images, and in more detail, PET images depicting the distribution of amyloid β protein in the brain. As one example, by using Pittsburgh compound B as a PET radiopharmaceutical (tracer) and using the reaction between the Pittsburgh compound B and amyloid β protein, it is possible to obtain PET images 72 depicting the distribution of amyloid β protein in the brain.

Accordingly, the actual Type-2 image data 72 in the present embodiment is an example of actual substance image data including distribution information that visualizes the distribution of a first substance related to an abnormality to be diagnosed. In the present embodiment, the abnormalities (diseases) to be diagnosed include Alzheimer's-type dementia, and the first substances that suggest the presence of disease include amyloid β protein. An SUVR value (Standardized Uptake Value Ratio or cerebellar SUVR), which indicates distribution of amyloid β protein in a set of parts of the brain, in more detail, the ratio between the sum of the accumulation (SUV, Standardized Uptake Value) of amyloid β protein in cerebral gray matter and the accumulation (SUV) of amyloid β protein in the cerebellum, is known as an index value for determining whether there is the risk of developing Alzheimer's-type dementia. SUVR can be defined by Equation (1) below.

$$SUVR = \frac{SUV(\text{frontal}) + SUV(\text{cingulate}) + SUV(\text{parietal}) + SUV(\text{temporal})}{SUV(\text{cerebellum})} \quad (1)$$

The numerator in Equation (1) represents the sum of the SUVs of the cerebral gray matter at the four sites, namely the cortical regions of the cerebrum (prefrontal cortex, anterior-posterior cingulate cortex, parietal lobe, and lateral temporal lobe) and the denominator indicates the SUV of the cerebellum.

Accordingly, when the reference region is the entire brain 81, the evaluation target region 82 for obtaining the SUVR as an index value includes five regions that are the prefrontal cortex, the anterior-posterior cingulate cortex, the parietal lobe, the lateral temporal lobe, and the cerebellum. Note that the SUV can be determined from the density of voxels (image elements, may be pixels) with a predetermined luminance or higher included in the PET image 72. As one example, in an ADNI database used as the training data 70 (see Susan Landau & William Jagust "Florbetapir processing methods" ADNI (Alzheimer's Disease Neuroimaging Initiative) Jun. 25, 2015), the amyloid positive/negative cutoff value is given as "1.11". In FIG. 2, the amyloid-positive parts are depicted with diagonal shading.

The images depicted on the third level (Row (c)) of FIG. 2 are mask images 73 indicating the evaluation target region 82, which has been set based on the MR images 71, and the images depicted on the fourth level (Row (d)) are the actual PET images 74 of the evaluation target region 82, which have been cut out based on the mask images 73. That is, the set of images depicted in Row (d) is the actual Type-2 image data 74 of the evaluation target region 82 and is included as information in the actual image 72. Although the positional relationship between the evaluation target region 82 and the reference region (i.e., the entire brain) 81 can be set using an ROI (Region Of Interest) template as disclosed in the Free Surfer Method (Gregory Klein, Mehul Sampat, Davis Staewen, David Scott, Joyce Suhy "Comparison of SUVR Methods and Reference Regions in Amyloid PET" SNMMI 2015 Annual Meeting, Jun. 6-10, 2015, Baltimore, MD, USA), the present invention is not limited to this method.

Figure 3:
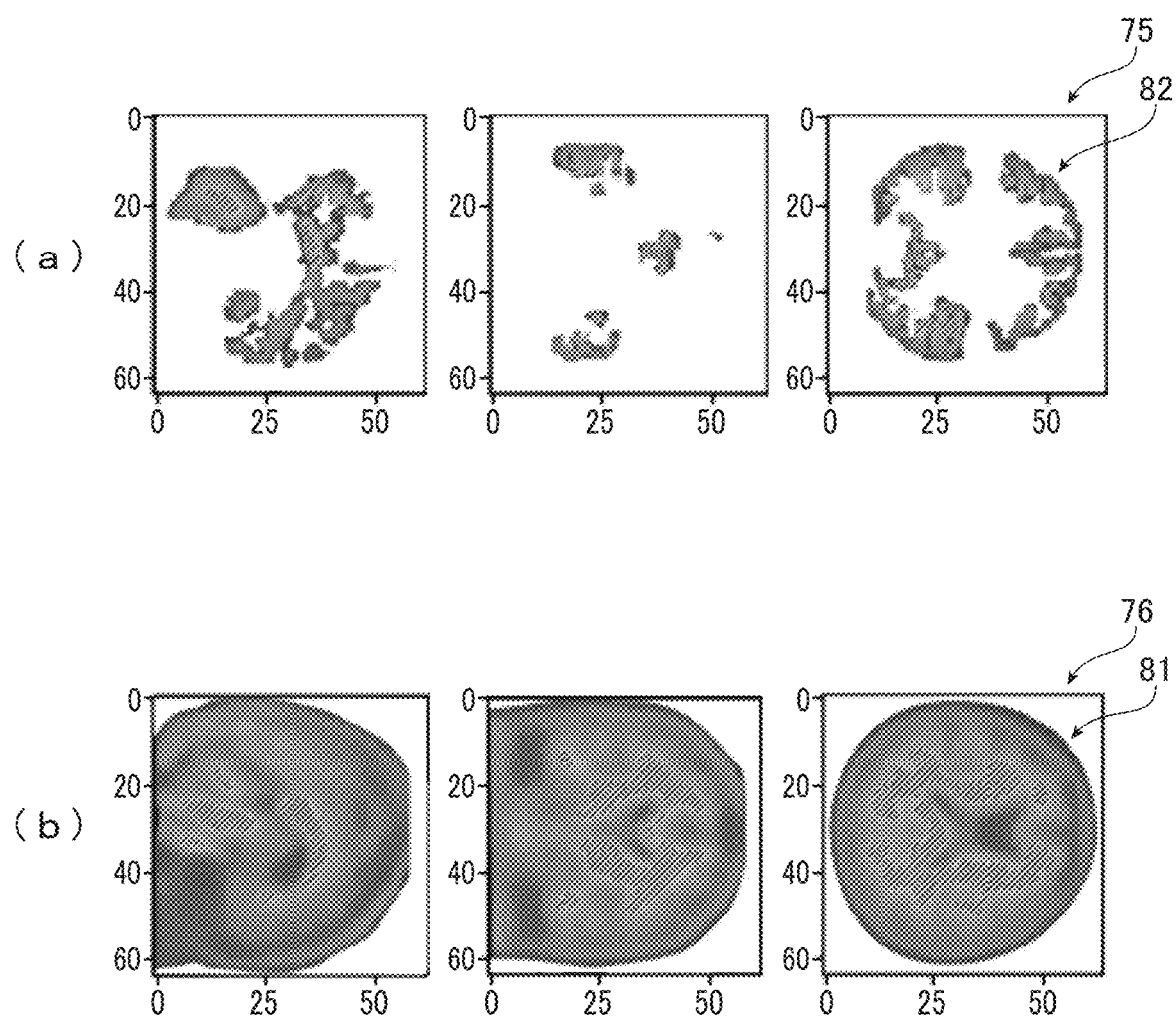
FIG. 3 is examples of images generated (estimated) by a model machine learned with the training data, where row (a) is pseudo PET images of a region of interest in the brain and row (b) is pseudo PET images of the entire brain.

FIG. 3 depicts pseudo Type-2 image data 75 of the evaluation target region 82 that has been generated by the machine learned image processing model 60. The upper level (Row (a)) in FIG. 3 depicts a set of pseudo Type-2 image data (pseudo-PET images or estimated PET images) 75, including the prefrontal cortex, anterior-posterior cingulate cortex, parietal lobe, lateral temporal lobe, and cerebellum that are the evaluation target region 82, which has been generated by the image processing model 60 from the set of the actual MRI (Type-1) images 71 of the reference region (i.e., the entire brain) 81. The lower level (Row (b)) in FIG. 3 depicts, for reference purposes, pseudo-PET images 76 of the entire brain 81 that have been generated by the other model that is built by machine learning to generate pseudo PET images of the reference region (i.e., the entire brain) 81 corresponding to the PET images, from the actual MR images 71 of the reference region (i.e., the entire brain) 81.

In the present embodiment, the image processing model (image generating model) 60, which is a model subject to machine learning, includes a model algorithm 61 and model parameter sets (or simply "parameters") 62. The learning unit (training unit) 53 of the model providing module 50 includes a first parameter learning function 54 that evaluates between a PET image 74, which is to be learnt, and a pseudo PET image 75, which is a learning result, based on a loss function Ei to learn the parameter set (parameters) 62 of the image processing model 60. One example of the loss function Ei is expressed by Equation (2) below.

$$Ei = \gamma * MSEi + (1-\gamma) * |Vi - predVi| \quad * * * \quad (2)$$

MSEi is the square error of image elements (that are corresponding to voxels or pixels), and is one example of an index for measuring the differences between image elements (voxels), that is, one example of a degree of deviation indicating the extent of deviation of values of image elements (voxels, may be pixels) in pseudo Type-2 image data (a pseudo PET image) 75 of an evaluation target region 82 from the values of the image elements in the actual Tyep-2 image data (PET image) 74 of the corresponding evaluation target region 82. The value of an image element in the actual image data (the PET image) 74 of an evaluation target region 82 is the same as the value of the image element in the evaluation target region 82 included in the actual image data (PET image) 72 of the reference region 81, so that voxel elements (may be pixel elements) in the pseudo PET image 75 may be compared with image elements in either of the PET images 72 and 74. As an index (degree of deviation) for measuring differences between voxel elements for optimization purposes, it is possible to use a different index such as SSIM (Structural Similarity) and PNSR (Peak Signal to Noise Ratio), either in place of the MSE or together with MSE.

The actual index value Vi is an actual index value (a real index value), for example, SUVR (actual SUVR, real SUVR) obtained from distribution information (SUV) of the first substance (for example, amyloid) in the evaluation target region 82 of the actual Type-2 image data (PET image data) 72, which is actual substance image data (real substance image data) including distribution information that visualizes the distribution of the first substance (amyloid) related to the abnormality to be diagnosed. This actual index value SUVR may be acquired from the PET image 74 of the evaluation target region 82. A pseudo index value predVi is a pseudo-index value, for example, a pseudo SUVR (estimated SUVR), obtained from pseudo distribution information corresponding to the distribution of the first substance (for example, amyloid) included in the pseudo Type-2 image data (pseudo PET image) 75 of the evaluation target region 82. That is, the pseudo index value is a SUVR value estimated from the MR image 71 using the image processing model 60. The pseudo distribution of the evaluation target region 82 is included in the pseudo PET image 75 as voxel information (image element information). This means that it is possible to obtain a pseudo SUVR from the pseudo PET image 75 using Equation (1) in the same way as the actual SUVR.

The loss function Ei indicated in Equation (2) includes the degree of deviation (square error) MSEi, the actual index value Vi (SUVR or actual SUVR), and the pseudo index value predVi (pseudo SUVR) and makes it possible to evaluate the image processing model 60 using these index values. The parameter learning function 54 of the learning unit 53 sets (or corrects or changes) one or more parameters 62 so that the index value MSEi included in the loss function Ei becomes smaller or the difference between the actual index value Vi and the pseudo index value predVi becomes smaller, and outputs the machine learned (trained) image processing model 60 including the trained parameters (machine learned parameter or parameters) 62 to the memory 102.

The coefficient γ included in the loss function Ei is a coefficient that satisfies the condition in Equation (3) below.

$$0 \leq \gamma \leq 1 \quad \ldots \quad (3)$$

When the coefficient γ is 0, the evaluation focuses on the difference between the actual index value Vi and the pseudo index value predVi when training the model 60. When the coefficient γ is 1, the evaluation focuses on the degree of deviation (square error) MSEi when training the model 60. In more detail, Equation (3) may be (0<γ<1) or even (0.5<γ<1.0). The image processing model 60 includes a function as an image output model that generates a second type image (Type-2 image) from a first type image (Type-1 image), and may preferentially evaluate correlations between image elements.

Figure 4:
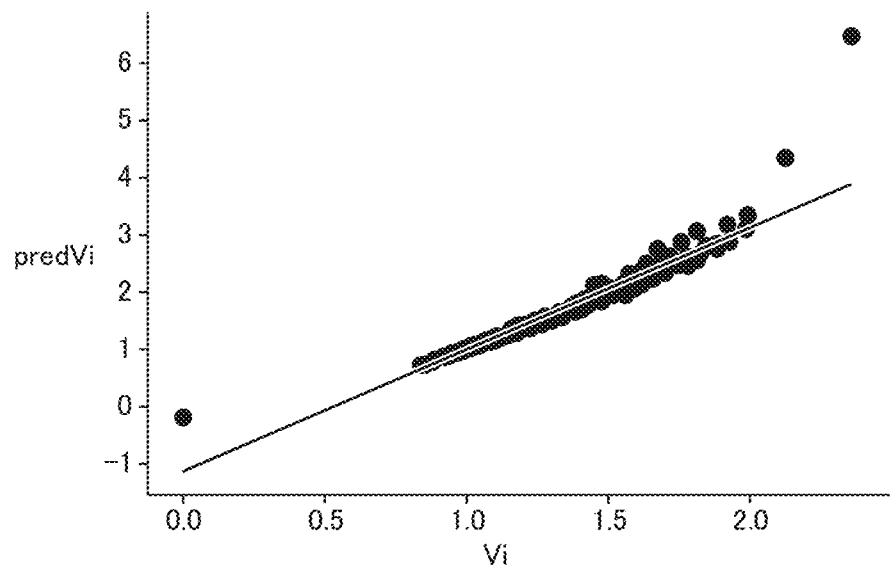
FIG. 4 is a graph in which the horizontal axis is an actual index value and the vertical axis is a pseudo index value, and each pair of an actual index value and a pseudo index value of a set of training data is displayed as one point.

In FIG. 4, pseudo index values predVi (predSUVR) of pseudo PET images 75 obtained when data sets of a plurality of test subjects included in the training data 70 are inputted into the machined learned image processing model 60 are depicted relative to actual index values Vi (SUVR). As indicated by the straight line produced by linear approximation in the drawing, it can be understood that the actual index values SUVR and the pseudo index values predSUVR have positive correlation and sufficiently high reproducibility. It can therefore be understood that the machine learned (trained) image processing model 60 is capable of estimating a PET image 75 from an MR image 71, and the machine learned image processing model 60 is also capable of estimating an SUVR value from an MR image 71.

Figure 5:
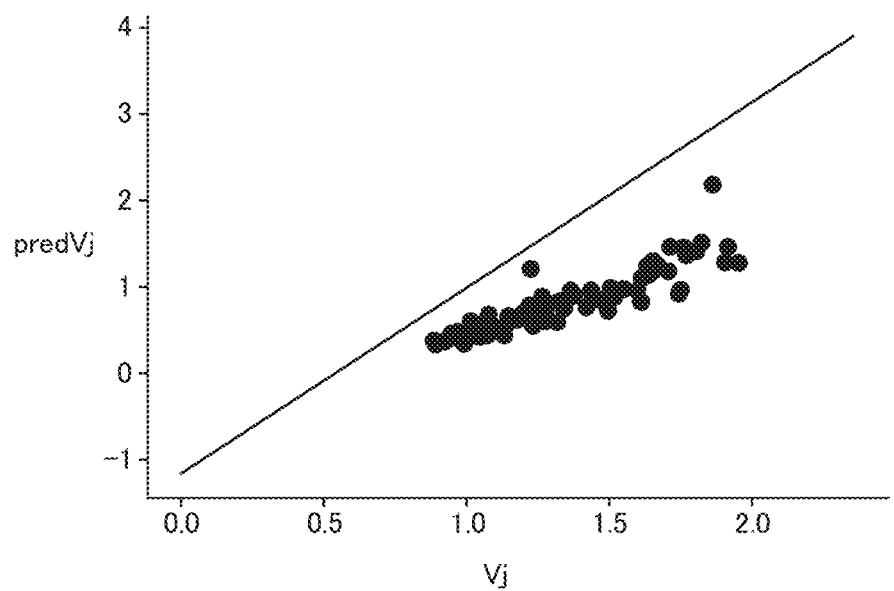
FIG. 5 is a graph in which the horizontal axis is the actual index value, the vertical axis is the pseudo index value, and each pair of an actual index value and a pseudo index value in of a set of test data is displayed as one point.

In FIG. 5, pseudo index values predVi (predSUVR) of pseudo PET images 75 obtained when data sets of a plurality of test subjects not included in the training data 70 are inputted as test data 79 into the machine learned image processing model 60 are depicted relative to the actual index values Vi (SUVR). Although the pseudo index values pred- SUVR recognized from pseudo PET 75 images generated by the machine learned image processing model 60 from the test data 79 tend to be smaller than the actual index values SUVR for the test data 79, it can be understood that there is also positive correlation between actual index values SUVR and the pseudo-index values predSUVR for the test data 79. This means that the machine learned (trained) image processing model 60 is capable of accurately estimating a PET image 75 from an MR image 71 of a target subject who has not been learned, and the machine learned image processing model 60 is also capable of accurately estimating an SUVR value from an MR image 71 of a target subject who has not been learned.

Figure 6:
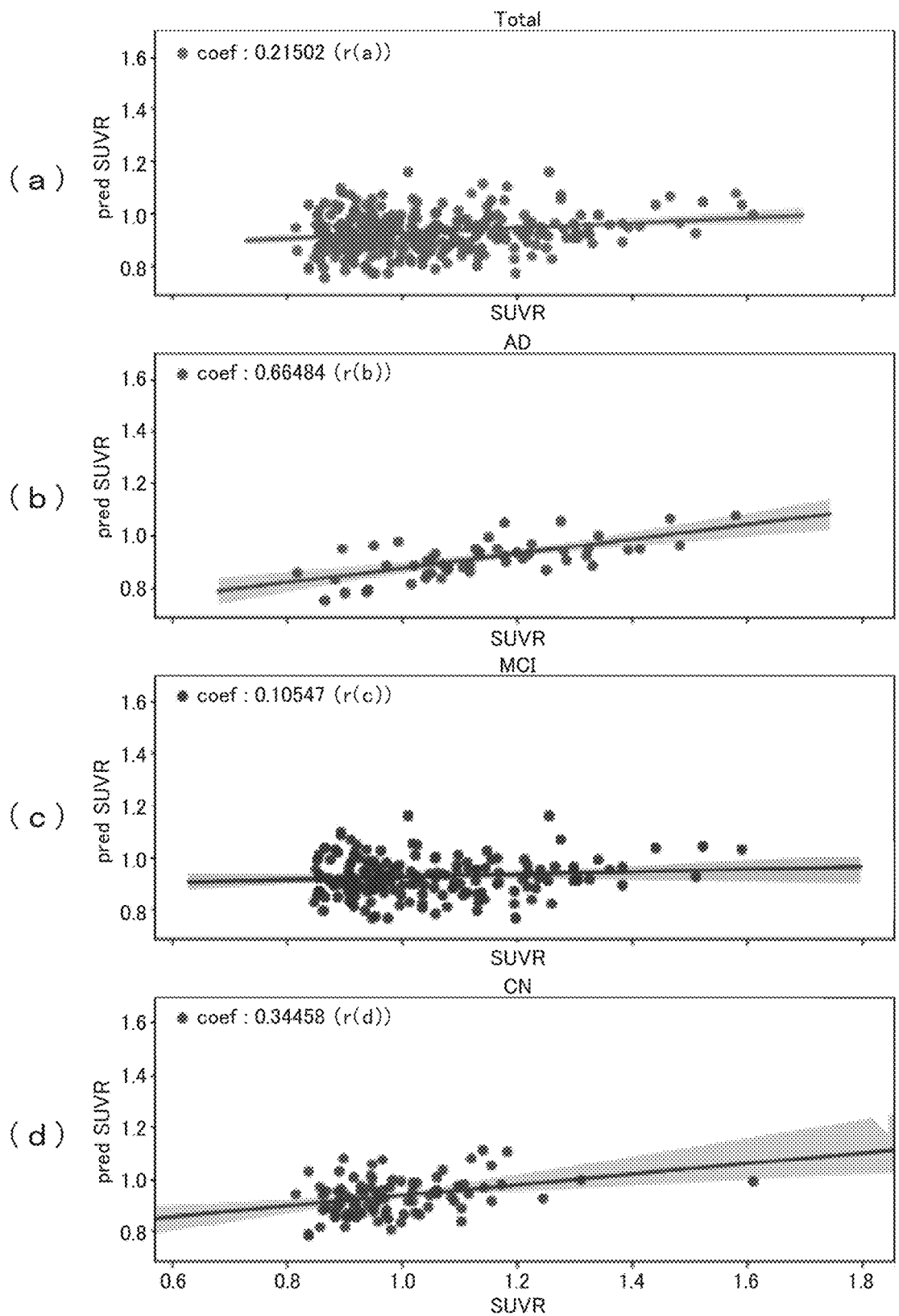
FIG. 6 depicts correlation between the pseudo SUVR (predSUVR) obtained from the pseudo PET image by a machine learned model to generate a pseudo PET of the evaluation target region and the SUVR value obtained from an actual PET image, where (a) depicts the correlation for all test subjects, (b) for test subjects diagnosed with AD, (c) for test subjects diagnosed with MCI, and (d) for test subjects of CN.

FIG. 6 depicts the correlation between the pseudo SUVR of pseudo PET images 75, which have been generated by the image processing model 60 machine learned to generate pseudo PET images 75 limited to (limited in) the evaluation target region 82 by using an MR image 71 as an input and using the SUVR as an index value for the loss function during learning, and SUVR values obtained from actual PET images 72 (74). The uppermost graph (a) depicts the data correlations for all test subjects, that is, subjects diagnosed with AD (Alzheimer's disease), subjects diagnosed with MCI (Mild Cognitive Impairment), and subjects found to be CN (Cognitive Normal). The next graph (b) depicts the data correlations for AD subjects, the graph (C) depicts the data correlations for MCI subjects, and the graph (d) depicts the data correlations for CN subjects. The correlation coefficient r(a) of the graph (a) is 0.21502, the correlation coefficient r(b) of the graph (b) is 0.66484, the correlation coefficient r(c) of the graph (c) is 0.10547, and the correlation coefficient r(d) of the graph (d) is 0.34458.

Figure 7:
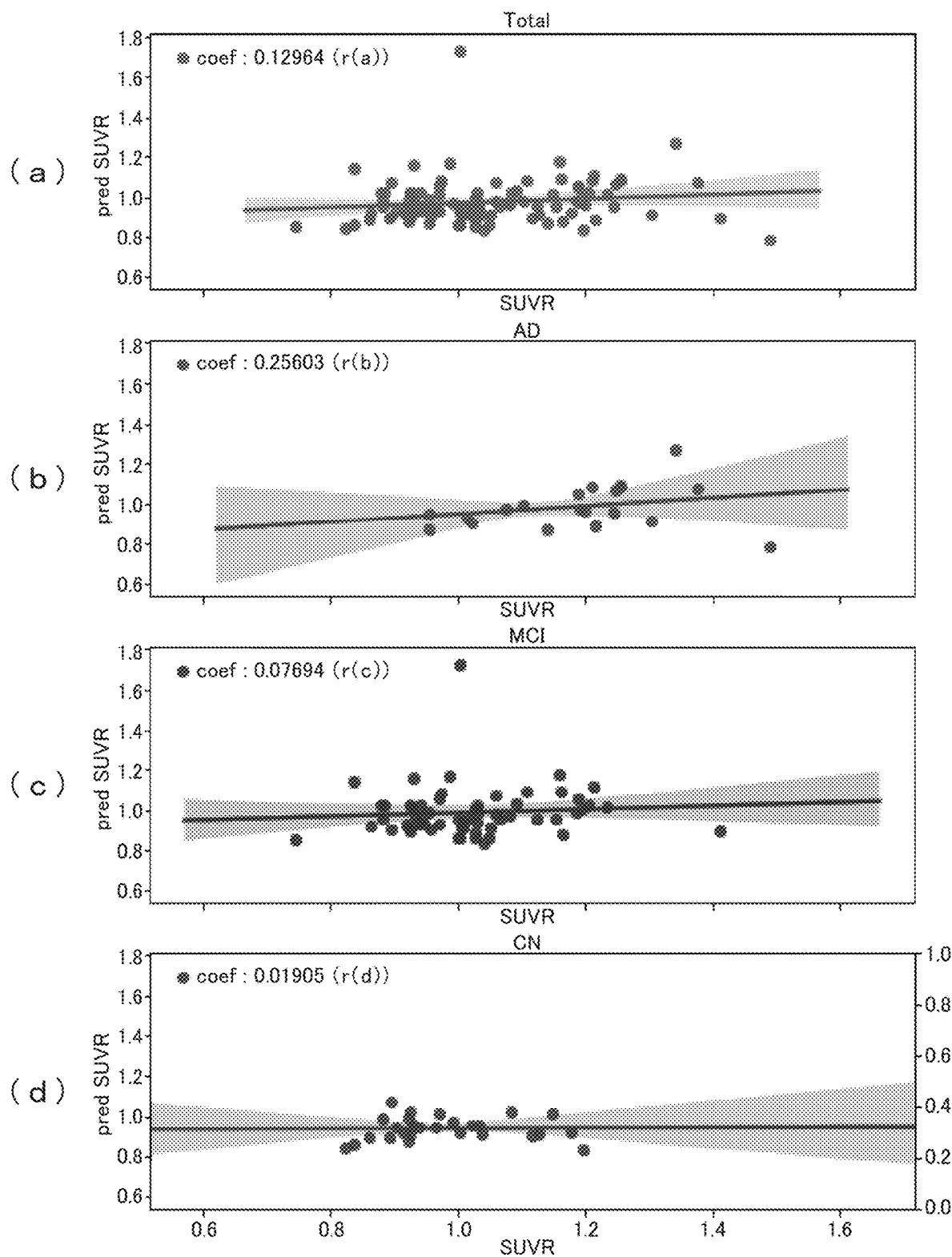
FIG. 7 depicts correlation between the pseudo SUVR (predSUVR) obtained from the pseudo PET image by a different machine learned model to generate a pseudo PET for the entire brain and the SUVR value obtained from an actual PET image, where (a) depicts the correlation for all subjects, (b) for AD, (c) for MCI, and (d) for CN.

FIG. 7 depicts, as a reference, results of the method used in the article produced by Sikka et al, that is, results of calculating SUVR from the amyloid PET images of the entire brain estimated by an image generating model built by simple machine learning with the method disclosed by Sikka et al., from MR images of the entire brain. Graphs (a) to (d) are the same as above. The correlation coefficient r(a) of the graph (a) is 0.12964, the correlation coefficient r(b) of the graph (b) is 0.25603, the correlation coefficient r(c) of the graph (c) is 0.07694, and the correlation coefficient r(d) of the graph (d) is 0.01905.

Accordingly, it can be understood that by generating pseudo PET images using the machine learned image processing model 60 according to the present embodiment, it is possible to significantly improve the estimation accuracy of SUVR, which is important as an index for dementia. Here, it is believed that one of factors for the performance of the image processing model 60 is that limiting the area in focus for generating (limiting the area for output) cancels out the influence of nonspecific accumulations that have reacted with substances aside from amyloid in the white matter of the brain. In addition, since the image processing model 60 generates, based on the MR image 71 that has the entire brain as its reference region 81, the pseudo PET image 75 of the evaluation target region 82 that is a part of the reference region 81, the amount of information in the MR image 71 used as a reference is sufficiently large relative to the pseudo PET image. This means that the pseudo PET image 75 of the evaluation target region 82 can be accurately generated based on a larger amount of information. This means that by using the image processing model 60 that has been machine learned as described above, it is possible to provide diagnosis support information 110 including an index that determines the progression of disease with high accuracy from an MR image (MRI) even when an actual PET image is not acquired from the target subject 5.

The learning unit 53 also includes a second parameter learning function 55 that learns the parameters 62 of the image processing model 60 including attribute information (property information) 90 of a plurality of test subjects. That is, the training data 70 includes attribute information 90 including information 91 related to biomarkers of the plurality of test subjects, in addition to the Type-1 and Type-2 image information 71 to 74 for the plurality of test subjects. The machine learned image processing model 60 is provided from the model providing module 50 as a model that has undergone machine learning based on the training data that includes the attribute information 90 in addition to the image information.

The attribute information 90 may include age, gender, educational history, work history, a cognitive test score (MMSE, CDR, ADAS-Cog, or the like) and medical interview results (an ADL interview or the like), in addition to information 91 related to biomarkers, that is, gene information (such as ApoE) 91$a$ and/or blood test results 91$b$. It is expected that by using the machine learned image processing model 60 with training data including the attribute information 90, a more accurate pseudo PET image 75 and pseudo SUVR can be obtained. The gene information 91$a$ and the blood test result 91$b$ are especially useful in improving the performance of the image processing model 60.

Figure 8:
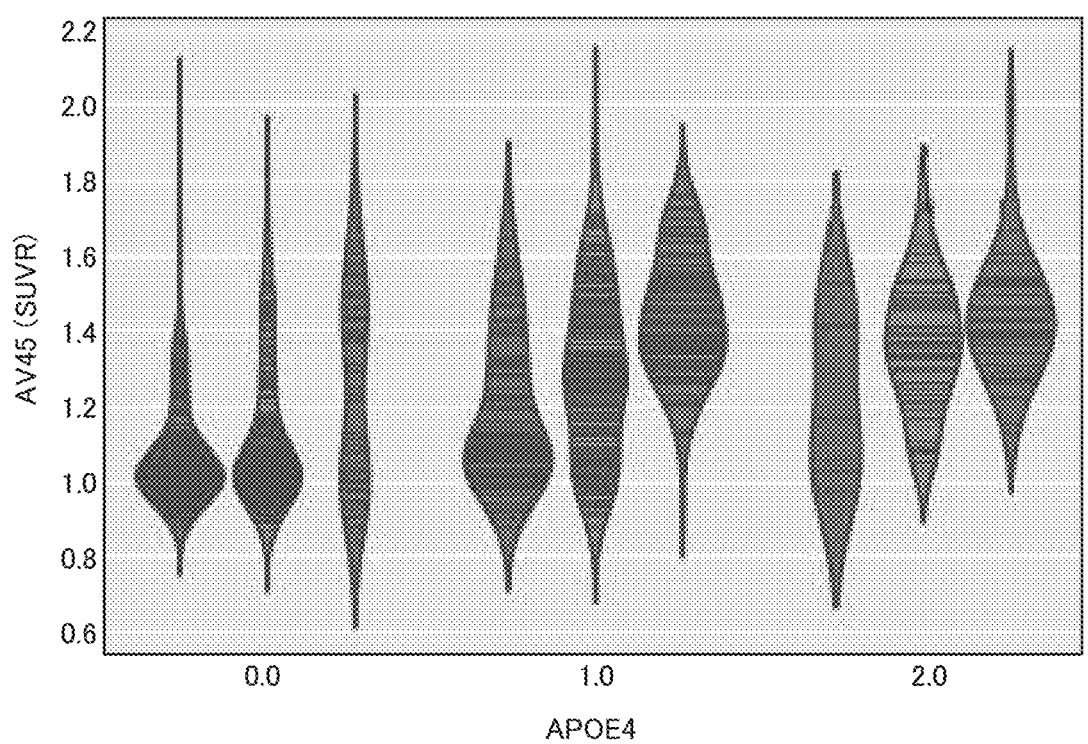
FIG. 8 is a diagram depicting correlation between genes and SUVR.

In the genetic information 91$a$, accumulation of amyloid β is believed to have high correlation with the amount of accumulation and the onset timing depending on the type of ApoE gene. As one example, FIG. 8 depicts the relationship between the ApoE gene type and the distribution of SUVR values produced by AV45 amyloid PET imaging, based on data in the ADNI database described above. As can be understood from the drawing, gene type is believed to be extremely useful information for determining amyloid positive or negative. However, there are individual differences in onset timing (timing of expression), and unlike images and blood, this information may not be suited on its own for evaluation at the present time.

In recent years, it has been indicated that a blood test result 91$b$ may also be useful in determining amyloid positive or negative. As one example, a method of extracting only amyloid β-related peptides by a method that measures time of flight (TOF) using MALDI (Matrix Assisted Laser Desorption/Ionization) on blood remaining after unadsorbed compounds have been discarded using magnetic beads has been proposed, and a method of estimating the amount of amyloid β accumulated in the brain with high accuracy has been provided (see "High performance plasma amyloid-β biomarkers for Alzheimer's disease", Nakamura et al. Nature. 8 Feb. 2018). According to the above reference, it has been reported that it is possible to determine amyloid positive or negative with high accuracy using a composite biomarker where, out of (1) $APP_{699-711}$, (2) $Aβ_{1-40}$, and (3) $Aβ_{1-42}$ measured in blood by IP-MS (Immunoprecipitation-Mass Spectrometry), the ratio between (1) and (2) and the ratio between (2) and (3) have been mathematically combined. Note that although the blood test result 91$b$ is effective for evaluation of the present state, unlike images, the blood test may not be suited on its own to comparing amounts of amyloid accumulation at different locations.

Figure 9:
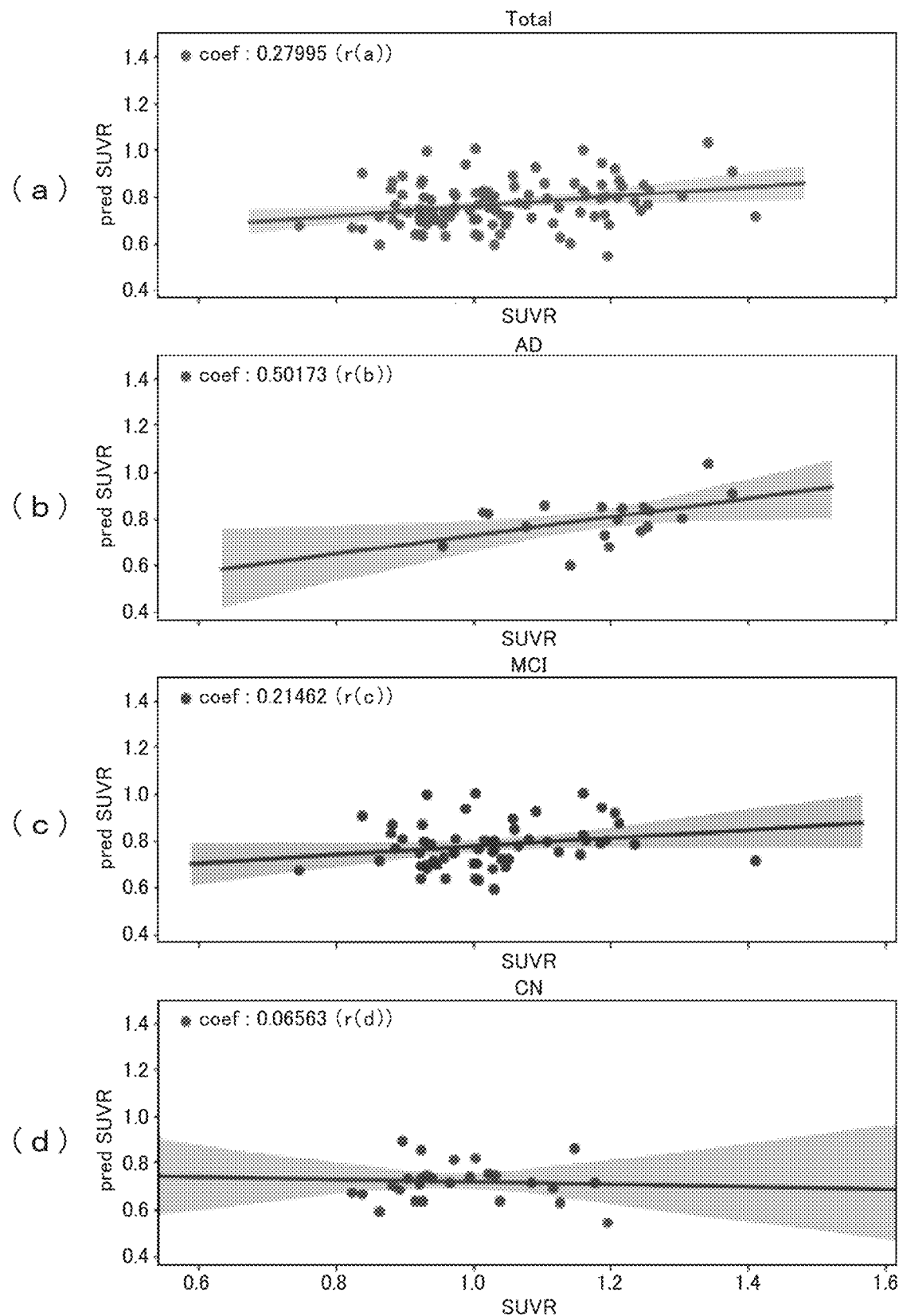
FIG. 9 depicts correlation between the pseudo SUVR (predSUVR) obtained from the pseudo PET image by a machine learned model to generate a pseudo PET including biomarkers and the SUVR value obtained from an actual PET image, where (a) depicts the correlation for all subjects, (b) for AD, (c) for MCI, and (d) for CN.

FIG. 9 depicts the correlation between the pseudo SUVR of pseudo PET images 75, which have been generated by the image processing model 60 machine learned (trained) to generate pseudo PET images 75 limited to (limited in) the evaluation target region 82, by using an MR image 71 and gene information (ApoE gene information) 91a as inputs and using the SUVR as an index value for the loss function during learning, and SUVR values obtained from actual PET images 72 (74). Graphs (a) to (d) are the same as FIG. 6 described above. The correlation coefficient r(a) of the graph (a) is 0.27995, the correlation coefficient r(b) of the graph (b) is 0.50173, the correlation coefficient r(c) of the graph(c) is 0.21462, and the correlation coefficient r(d) of the graph (d) is 0.06563. Compared to FIG. 6, the correlation between the SUVR values for all test subjects is improved, and the effect of learning including gene information can be seen for MCI subjects in particular. For this reason, it can be understood that the index value (SUVR value) for determining the degree of disease progression can be estimated with higher accuracy by using a model 60 which has performed learning based on the training data that includes attribute information 90 including biomarkers 91 such as genes. In particular, for target subjects 5 who are determined to be MCI, where care is needed regarding the progress of the disease, improving the estimation accuracy of the index value is valuable when providing the diagnosis support information 110, Note that although an SUVR value based on the cerebellum is used in the above description, if the influence of non-specific accumulation due to non-amyloid reactions can be eliminated, it is also possible to perform machine learning on PET images that are limited to other evaluation target regions 82 and improve the learning accuracy using index values based on other evaluation regions.

In this way, the machine learned image processing model 60 provided by the model providing module 50 is capable of accurately estimating PET images 75, which include information relating to the distribution of amyloid and the like indicating the cause or progression of a disease, based on image data, like an MR image 71 or the like, which is capable of mainly acquiring information relating to morphology inside the living body but does not use a medicine (although a contrast agent or the like may be used to clarify the morphology). For this reason, the information providing unit 12 of the diagnosis support module 10 is capable, using the image processing model 60, of generating (estimating), based on MR images (MRI, individual actual image data or actual MR images) 15 included in the subject information 105 acquired from the target subject 5 via the acquisition unit 11, pseudo PET images (pseudo image data of the target region) 115 that is limited to the evaluation target region 82 and capable of providing the diagnosis support information 110 including the pseudo PET image 115 and/or an SUVR value (pseudo index value) 116 of the evaluation target region 82 obtained from the pseudo PET image 115.

In the example described above where part of the brain is used as the evaluation target region 82, the evaluation target region 82 includes a plurality of locations in the brain, in more detail, as depicted in FIG. 2 and the like, five parts (locations) composed of the prefrontal cortex, the anterior-posterior cingulate cortex, the parietal lobe, the lateral temporal lobe, and the cerebellum, and the SUVR value, which is the actual index value is calculated as indicated in Equation (1) from distribution information for the plurality of locations. In the information providing unit 12, the pseudo PET image 115 generated by the image processing model 60 based on the MR image 15 of the target subject 5 includes these five regions as the evaluation target region 82. Accordingly, it is possible for the information providing unit 12 to calculate the pseudo SUVR 116 from the distribution information of the five corresponding regions included in the evaluation target region 82 of the pseudo PET image 115 and provide the pseudo SUVR 116 as diagnosis support information 110.

The acquisition unit 11 of the diagnosis support module 10 may be configured to acquire the subject information 105, which includes the attribute information 14 including information relating to biomarkers, and the information providing unit 12 may estimate, based on individual image data (MR images) 15 and attribute information 14 of the target subject 5, the pseudo image data (pseudo PET) 115 of the evaluation target region 82 using the image processing model 60 that has been machine learned with the data including the attribute information 90 and may provide the diagnosis support information 110 based on this information. The attribute information 14 included in the subject information 105 may include all of the information included in the attribute information 90 described above or may include only part of this information. As one example, the attribute information 14 may include information 91 relating to biomarkers in the form of the gene information 91a and/or blood test result 91b.

In addition, the image processing model 60 may be machine learned (trained) to derive a diagnosis result for an abnormality to be diagnosed, that is, a diagnosis result for a disease, from the MR image 71, and the information providing unit 12 may provide the diagnosis support information 110 which includes an estimated diagnosis result (pseudo-diagnosis result) 117. In this case, the training data 70 includes, in addition to the image data 71 to 74 for a plurality of test subjects, diagnosis results 94 of an abnormality to be diagnosed for the test subjects, for example, dementia. The learning unit 53 provides the image processing model 60 machine learned to estimate a diagnosis result (medical condition) 95 in addition to the pseudo PET image data 75 from the MR image data 71 indicating the morphology. The information providing unit 12 uses the machine learned image processing model 60 to provide the diagnosis support information 110 that includes the pseudo-diagnosis result 117 including the abnormality to be diagnosed for the target subject 5, which has been estimated from the information included in the subject information 105.

Note that the information providing function 12 of the diagnosis support module 10 may be included in the terminal 20 of the medical institution 200, and by implementing the machine learned image processing model 60 in advance, the diagnosis support information 110 can be provided as a stand-alone system (apparatus). Also, although the image processing model 60 is described as having been trained in the above description, the machine learned image processing model 60 may perform self-learning continuously based on new cases at any time, and an image processing model 60 that has been updated by the model providing module 50 may be automatically provided.

The image processing model 60 may perform machine learning in the same way as described above based on training data (learning data or teaching data) 70 which includes different image types (modalities) and estimate, with high accuracy, images of another modality aside from amyloid PET images indicating the distribution of amyloid β. As one example, the accumulation of tau protein (tau) is thought to be directly linked to the death of nerve cells in dementia, and in recent years, it has become possible to acquire PET images (tau PET) using medicines such as PBB3 to visualize the accumulation of tau protein. At present, a cerebellar-based SUVR value is often used in the same way as described above to evaluate the distribution of tau protein, but it is also possible that other evaluation target regions 82 come under focus. The estimation of FDG (fluorodeoxyglucose) PET images can also be supported in the same way by a machine learned (trained) image processing model 60 where FDG-PET images have been included in the training data 70. Also, in place of MR image data, CT image data may be used as the Type-1 image data 71, which mainly includes the morphological information, to train the image processing model 60. Another modality that can be supported by an image processing model 60 of this invention is SPECT images. As one example of SPECT images, there is an imaging method that visualizes the distribution of a dopamine transporter (DAT) called DatS-CAN (Dopamine transporter SCAN) in a SPECT test where a radiopharmaceutical called $^{123}$I-Ioflupane is administered. Example objects for this type of imaging include early diagnosis of parkinsonisms (PS) in Parkinson's disease (PD), to assist in diagnosis of dementia with Lewy bodies (DLB), and decisions over medication with levodopa in the presence of striatal dopaminergic nerve loss. With DatS-CAN imaging, there is a waiting time of three to six hours for the diagnostic agent to reach the brain, and while there are few side effects, the process is invasive and is relatively expensive even when health insurance is applied. The ability to easily estimate from MRI images whether such testing is necessary is therefore valuable in reducing the burden placed on patients.

The BR (Binding Ratio) or SBR (Specific Binding Ratio) is used as an index value for DatSCAN evaluation and is expressed by Equation (4) below.

$$BR = \frac{C_{specific} - C_{nonspecific}}{C_{nonspecific}} \quad (4)$$

The item "C" in Equation (4) is the mean value of DAT in each region of interest, "$C_{specific}$" is the mean value of the putamen and caudate nucleus in the brain, and "$C_{nonspecific}$" is the mean value of the occipital cortex in the brain. Accordingly, in the model providing module 50, it is possible to provide the machine learned image processing model 60 based on training data 70 including MR images of the entire brain as the actual Type-1 image data 71 of the reference region 81 for a plurality of test subjects and SPECT images including the putamen, caudate nucleus, and occipital cortex in the brain as the actual Type-2 image data 72 (74) including the evaluation target region 82, so as to generate a pseudo SPECT image 75 including the putamen, caudate nucleus, and occipital cortex, which are the evaluation target regions 82, from an MR image 71.

The diagnosis support module 10 is capable of generating, using the machine learned image processing model 60, a pseudo SPECT image 115, which is pseudo Type-2 image data of the evaluation target region 82, from an MR image or CT image 15 of the subject 5, which is individual actual Type-1 image data to be examined, and of providing the diagnosis support information 110 which includes a pseudo BR value (or pseudo SBR value) as a pseudo index value based on the pseudo SPECT image 115. Differences between pixels and BR, which is an index value, are used in the loss function (loss) Ei used during machine learning of the image processing model 60, and the regions used for calculating this information are narrowed down to the putamen, caudate nucleus, and occipital cortex, which makes it possible to optimize the parameters 62.

Figure 10:
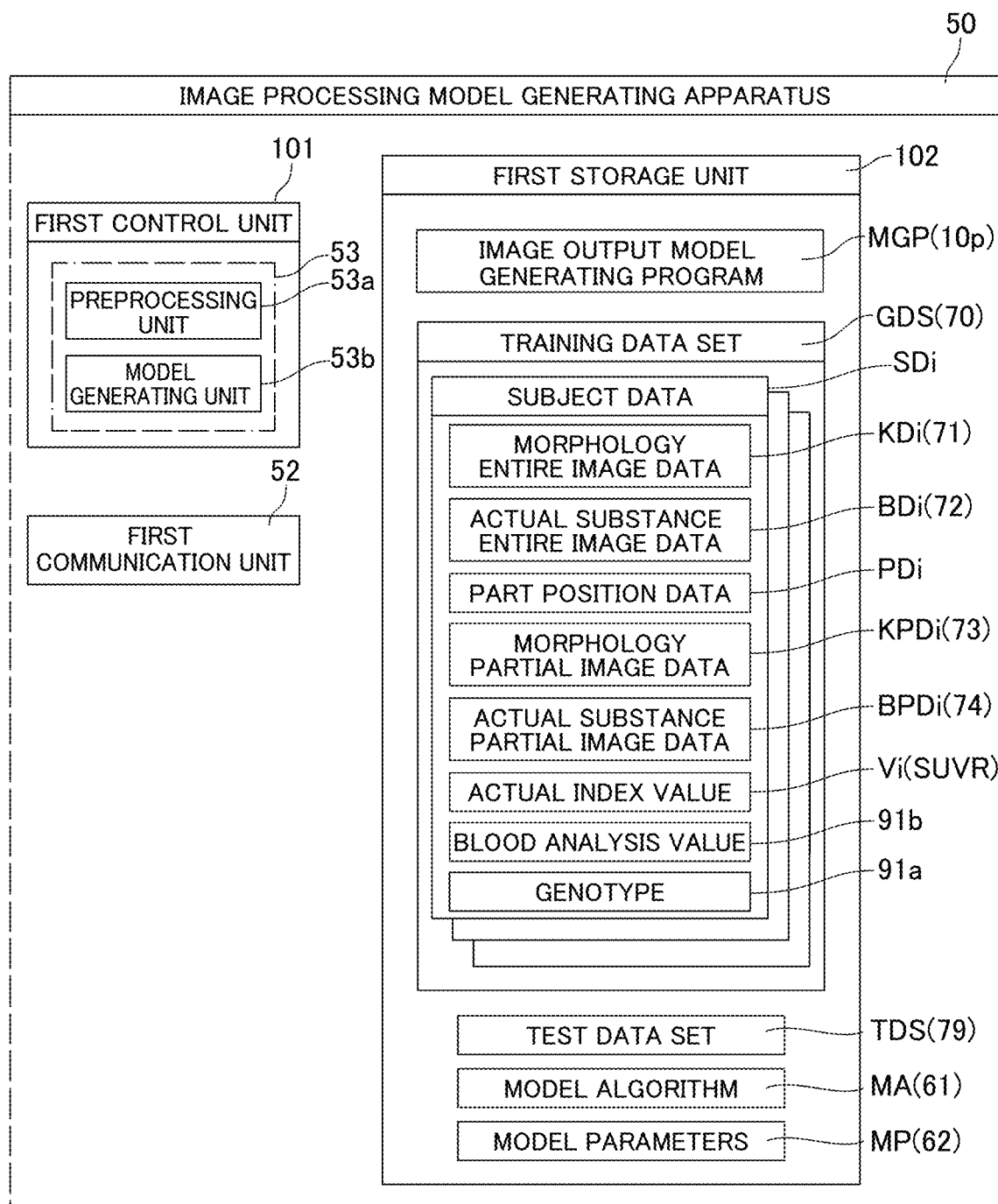
FIG. 10 is a block diagram depicting an overview of an image processing model generating apparatus.

The respective apparatuses will now be described further. FIG. 10 depicts the model providing module (image output model generating apparatus) 50. The generating apparatus 50 includes a first control unit 101, a first storage unit 102, and a first communication unit (communication interface) 52. The first control unit 101 is configured to be capable of exchanging data by transmitting and receiving signals to and from the first storage unit 102 and the first communication unit 52. The first communication unit 52 is configured to be capable of communicating with various external devices, such as a hospital terminal 210, via a diagnosis support system 100 or the Internet 9 via a network that uses wired or wireless communication. The first control unit 101 is composed, for example, of a computational processing device, such as a CPU (Central Processing Unit), a cache memory, an I/O device, and the like. The first control unit 101 functions as the learning unit 53, which includes a preprocessing unit 53a and a model generating unit 53b, by downloading and executing an image output model generating program MGP (50p) that is stored in the first storage unit The first storage unit 102 may be composed, for example, of a main storage device, such as a memory, and an auxiliary storage device, such as an HDD. The first storage unit 102 is configured to store the image output model generating program 10p, the training data set GDS (70), the test data set TDS (79), the model algorithm MA (61), and the model parameter set MP (62).

The training data set GDS (70) stores N sets of (where "N" is a natural number of 2 or higher) different subject data SDi (where "i" is a number that identifies the subject to whom the data relates and is such that 1≤i≤N). In the following description, the test subject to whom the set of subject data SDi relates will be referred to as appropriate as "test subject i". As one example, N is 300.

The subject data SDi of the training data set GDS (70) includes morphological entire image data KDi (71), actual substance entire image data BDi (72), morphological partial image data KPDi (73), actual substance partial image data BPDi (74), and the actual index value Vi (SUVR). The training data set 70 may include part position data PDi, which is a template (mask) for extracting the morphological partial image data 73 and the actual substance partial image data 74. Out of the subject data SDi, the part position data PDi, the morphological partial image data KPDi, the actual substance partial image data BPDi, and the actual index value Vi may be values that are identified by the first control unit 101 during execution of the image output model generating program MGP and may be values that are not stored before the execution of the image output model generating program MGP.

As depicted in FIG. 2, one example of the morphological entire image data KDi (71) is data produced by image pickup of one or a plurality of parts of the body of the test subject i, in more detail, the morphology in the brain, using a predetermined method such as CT or MRI. The morphological entire image data KDi is an MRI of the entire brain, The morphological entire image data KDi (71), which is the actual Type-1 image data of the reference region, is 3D data of a predetermined size (for example, 64×64×64). The morphological entire image data KDi can be expressed by a combination of a number (in keeping with a predetermined size, and for example, 64×64×64) of image elements (in the present embodiment, voxels) indicating values (luminance values) indicating luminance. The morphological entire image data KDi may be expressed by a combination of a number (in keeping with a predetermined size and for example, 64×64×64) of image elements (in the present embodiment, voxels) indicating colors (RGB values). Since the positions of these image elements can be expressed for example by three-dimensional coordinates, each image element of the morphological entire image data KDi is expressed as appropriate as KDi (x,y,z).

As depicted in FIG. 2, the actual substance entire image data BDi (72), which is the actual Type-2 image data including the evaluation target region, is data that visualizes the distribution of the target substance in one or more parts of the body of the test subject i, in more detail, the brain, using a predetermined method such as PET. The actual substance entire image data BDi is 3D data of same size as the morphological entire image data KDi. One or both of the actual substance entire image data BDi and the morphological entire image data KDi may be manipulated or standardized so that the positions on the image of each of the one or plurality of parts indicated in the actual substance entire image data BDi match the positions on the image of corresponding parts in the morphological entire image data KDi. FIG. 2 depicts cross-sectional views of a set of the actual substance entire image data BDi (72) at locations corresponding to respective cross-sectional views of the morphological entire image data KDi (71). In the actual substance entire image data, a value (or "luminance value") indicating the luminance of an image element (or "voxel") where the substance in question is present is a predetermined value or higher. Since the positions of these image elements can be expressed by three-dimensional coordinates for example, in the following description, each image element in the actual substance entire image data BDi is expressed as appropriate as BDi (x,y,z). Note that the target substance visualized by a PET image may be a substance that reacts with a tracer, or may be the tracer itself. Also, aside from a PET image depicting the distribution of amyloid β protein, a PET image depicting the distribution of tau protein may be used.

The part position data PDi is data indicating the position in each image of one or a plurality of parts (evaluation target regions, for example, cerebral gray matter and the cerebellum) 82 of the test subject i indicated in the morphological entire image data KDi. The part position data PDi may be expressed by parameters indicating the part of the test subject i to which each image element KDi (x,y,z) composing the morphological entire image data KDi belongs. In addition to or in place of this, the part position data PDi relating to one part may be expressed, for example, by parameters indicating a region in a three-dimensional coordinate system, or by a set of coordinates in a three-dimensional coordinate system.

As depicted in FIG. 2, the morphological partial image data KPDi (73) is partial image data obtained by extracting a predetermined part (evaluation target region) 82 from the morphological entire image data KDi (71) depicting the entire reference region 81. FIG. 2 depicts a set of cross-sectional views of the morphological partial image data KPDi (73) at locations corresponding to respective cross-sectional views of the morphological entire image data KDi (71).

As depicted in FIG. 2, the actual substance partial image data BPDi (74) is partial image data obtained by extracting portions corresponding to the morphological partial image data KPDi (73) from the actual substance entire image data BDi (72). FIG. 2 depicts a set of cross-sectional views of the actual substance partial image data BPDi at locations corresponding to respective cross-sectional views of the actual substance entire image data BDi. In the actual substance partial image data BPDi (74), in the same way as the actual substance entire image data BDi, values (luminance values) indicating the luminance of image elements (voxels) where the target substance is present are a predetermined value or higher. Values (RGB values) indicating the color of image elements where the target substance is present may be values (RGB values) indicating a color which is a predetermined color (for example, yellow), Since the positions of these image elements can be expressed by three-dimensional coordinates for example, in the following description, in the same way as the actual substance entire image data BDi, each image element in the actual substance partial image data BPDi is expressed as appropriate as BPDi (x,y,z).

The actual index value Vi is an index value for determining whether the test subject i is at risk of developing a certain disease, for example, Alzheimer's type dementia. As one example, the actual index value Vi is an SUVR value indicates the ratio of the extent of accumulation of amyloid β protein in the cerebral gray matter to the extent of accumulation of amyloid β protein in the cerebellum, which are recognized based on the actual substance partial image data BPDi. Note that the SUVR value may indicate the ratio of the degree of tau protein accumulation in the cerebral gray matter to the degree of tau protein accumulation in the cerebellum.

As examples, the blood analysis value BLi (91b) is a value, such as Hba1c (blood glucose level), measured in a blood test of the test subject i and/or values such as numerical values obtained based on the result of mass spectrometry of the test subject i's blood using IP-MS (immunoprecipitation mass spectrometry). The blood analysis value BLi may be a composite biomarker where, out of (1) $APP_{699-711}$, (2) $A\beta_{1-40}$, and (3) $A\beta_{1-42}$ that have been measured by mass spectrometry, the ratio of (1) $APP_{699-711}$ to (2) $A\beta_{1-40}$ and the ratio of (2) $A\beta_{1-40}$ to (3) $A\beta_{1-42}$ have been mathematically combined. As examples, the blood analysis value BLi may be a value such as HbA1c (blood glucose level) measured by a blood test in a typical examination or a value determined based on mass spectrometry.

The genotype GEi (91a) is a value based on a genotype which is composed of two sets of alleles of the test subject i. As one example, the genotype GEi is a value based on the genotype of the APOE gene that has three alleles ε2, ε3, and ε4. As specific examples, the genotype GEi is a discrete value of 0 to 2 that is 2 for a genotype with two ε4, 1 for a genotype with one ε4, and 0 for a genotype with no ε4. As another example, the genotype GEi may also be a discrete value of 0 or 1 where a case where one or more APOE genes ε4 are present is positive (=APOE4+=1) and the other cases are negative (=APOE4−=0).

In the same way as the training data set GDS (70), the test data set TDS (79) stores M (where M is a natural number of 1 or higher) different subject data SDj (where j is a number that identifies the test subject related to the data, such that 1≤J≤M). In the following description, the test subject (patient) related to the subject data SDj data is referred to as appropriate as test subject j. As one example, M is 75. Since the subject data SDj of the test data set TDS is the same data as the subject data SDi of the training data set GDS, description and illustration are omitted here. In the following description, "j" is added as appropriate to the symbol of each set of data included in the subject data SDj of the test data set TDS, as in the example expression "the morphological entire image data KDj in the test data set TDS".

The model algorithm MA (61) is information for specifying the algorithm to be used in the image output model. As an example, the information for specifying the algorithm to be used in the image output model is a machine learning library, such as TensorFlow, and also information such as the number of layers in a multi-layer convolutional neural network realized by the library, the functions to be used on the input layer, the hidden layer, and the output layer, and the number of functions on each layer. The model parameter set MP (62) is a set of parameters that define the operation of an algorithm used in the image output model. One example of the parameters are coefficients that are multiplied by the input values of the respective functions.

Figure 11:
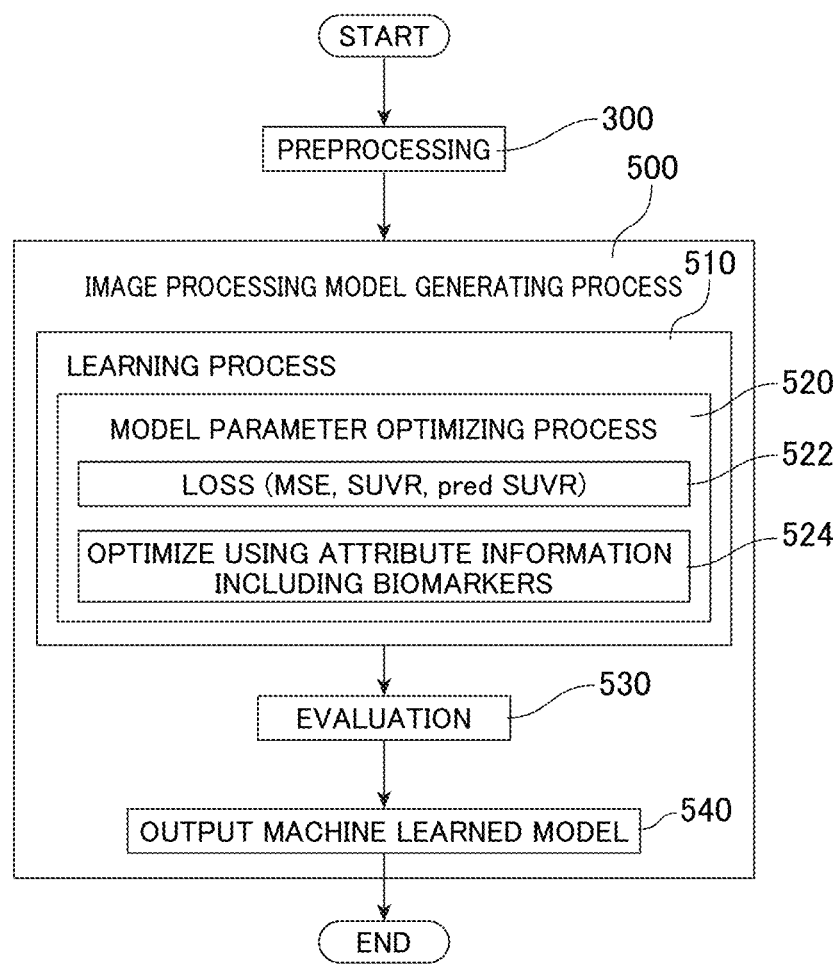
FIG. 11 is a flowchart depicting an overview of a generation process for an image processing model.

In FIG. 11, an overview of the processing in the model providing module (image processing model generating apparatus) 50 is depicted by way of a flowchart. In step 300, the training data 70 for training the image processing model 60 is prepared (preprocessing). In step 500, the image processing model 60 is generated and outputted. Step 500 includes a step (learning process) 510 of training (machine leaning) the image processing model 60 to generate the pseudo Type-2 image data (a pseudo PET image) 75 of the evaluation target region 82 from the actual Type-1 image data (actual image data of an MR image) 71 of the reference region 81 based on the training data 70.

The learning process (training process) 510 includes a process (model parameter optimizing process) 520 that learns optimal parameters (model parameters) 62 for the image processing model 60. The model parameter optimizing process 520 includes a step 522 of learning the parameters 62 of the image processing model 60 so that the difference between the actual index value (SUVR) and the pseudo index value (pseudo SUVR) becomes smaller using the loss function Ei including the actual index value (SUVR), which is obtained from the distribution information (SUV) of the first substance (for example, amyloid) in the evaluation target region 82 of the actual Tyep-2 image data (PET image) 72, and the pseudo-index value (pseudo-SUVR), which is obtained from pseudo-distribution information (pseudo-SUV) corresponding to the distribution of the first substance included in the pseudo Type-2 image data (pseudo-PET image) 75 of the evaluation target region 82. In this step 522, the loss function Ei may include a degree of deviation (for example, the square error MSE) indicating the extent of deviation of the values of the voxel elements of the pseudo Type-2 image data (pseudo PET image) 75 of the evaluation target region 82 from the values of image elements in the actual Type-2 image data (PET image) 74 of the evaluation target region 82.

In addition, the learning process 510 may include a step 524 that learns the parameters 62 of the image processing model 60 using the attribute information 90 including the information 91 related to biomarkers of a plurality of test subjects included in the training data 70. The biomarkers 91 may include at least one of information 91*b* obtained by analyzing the blood of each of a plurality of test subjects and information 91*a* based on genotypes. In addition, the model algorithm 61 that is optimized by the learning process 510 may have a convolutional neural network architecture, and step 524 that performs optimization using the attribute information may include the step that performs learning the parameters 62 of the image processing model 60 by including the attribute information 90 to the features of the convolutional neural network architecture.

In step 530, the image processing model 60 whose parameters have been optimized by the learning process 510 is evaluated using the test data 79, and in step 540, the trained image processing model (machine learned image processing model) 60 is provided so that it can be used by the diagnosis support module 10.

Figure 12:
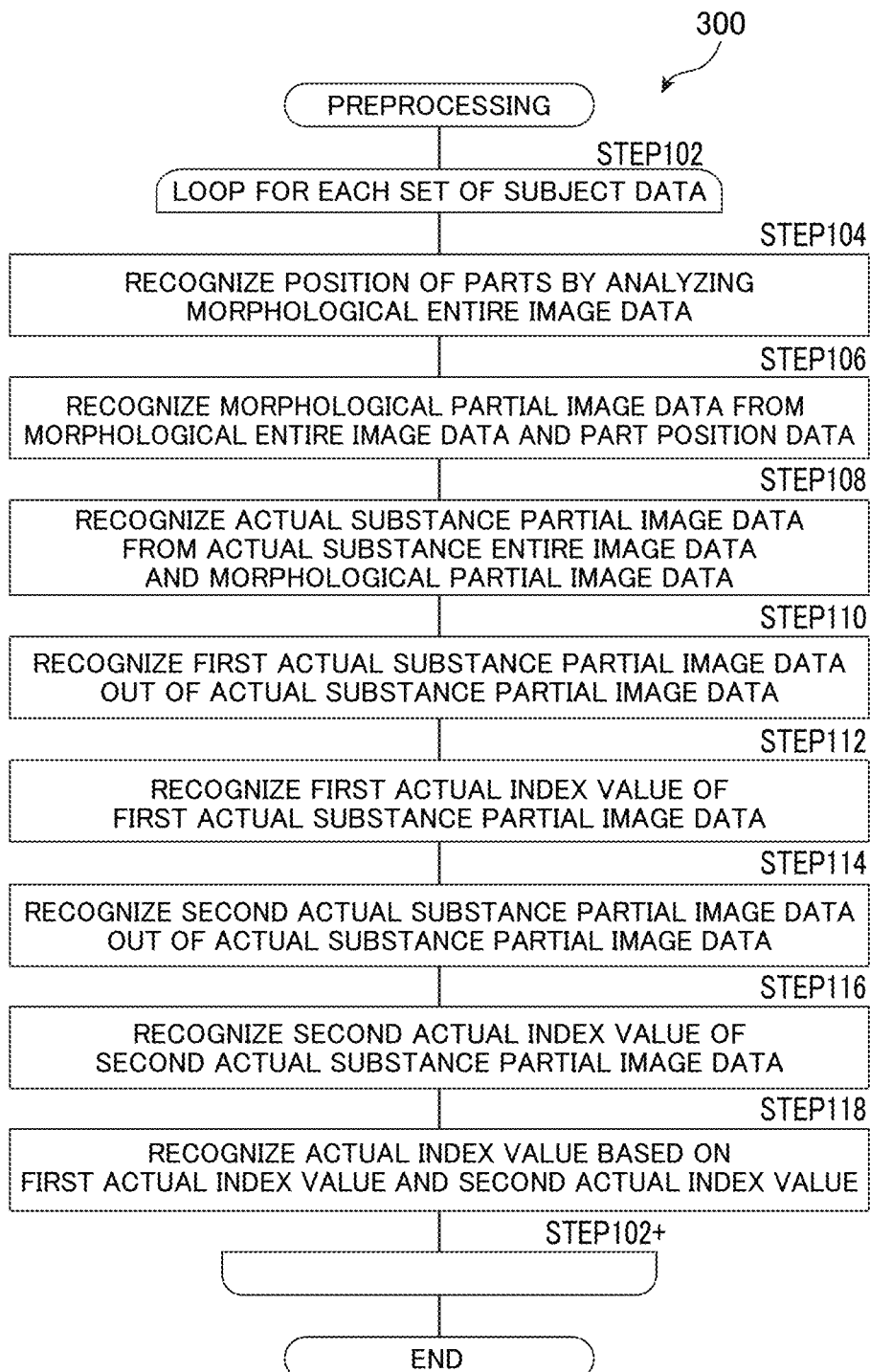
FIG. 12 is a flowchart depicting an overview of preprocessing.

FIG. 12 depicts an overview of the processing included in the preprocessing 300. The preprocessing unit 53*a* executes the processing in STEP 104 to STEP 118 for each set of subject data SDi in the training data set GDS (70) and each set of subject data SDj in the test data set TDS (STEP 102). In the following description, "k" is added to the symbol of the data to be processed as in the example expression "subject data SDk". The test subject (patient) related to the data is also indicated as the "test subject k".

The preprocessing unit 53*a* recognizes the positions in the Image of each part in the body of the test subject k by analyzing the morphological entire image data KDk (71), generates the part position data PDk, and stores the data in the first storage unit 102 (STEP 104).

As one example, by comparing template morphology entire image data indicating the shape, position, and luminance of typical human body parts with the morphological entire image data KDk, the preprocessing unit 53*a* attaches labels to the image elements KDk (x,y,z) that construct the morphological entire image data KDk to indicate the body parts of the test subject k, thereby generating the part position data PDk. As one example, the preprocessing unit 53*a* assigns labels indicating one of "cerebral gray matter", "cerebellum", "white matter with many nonspecific bindings", and "blank region" to each image element KDk (x,y,z) constructing the morphological entire image data KDk to generate the part position data PDk.

The preprocessing unit 53*a* recognizes the morphological partial image data KPDk (73) based on the morphological entire image data KDk and the part position data PDk, and stores the morphological partial image data KPDk (73) in the first storage unit 102 (STEP 106). As one example, the preprocessing unit 53*a* recognizes the morphological partial image data KPDk (73) by blanking out the partial image data of parts that have been labeled as "white matter with many nonspecific bindings" indicated in the part position data PDk from the morphological entire image data KDk (71).

The preprocessing unit 53*a* recognizes the actual substance partial image data BPDk (74) by extracting the partial image data of parts indicated in the morphological partial image data KPDk (73) from the actual substance entire image data BDk (72) and stores the actual substance partial image data BPDk (74) in the first storage unit 102 (STEP 108). Based on the part position data PDk, the preprocessing unit 53*a* recognizes first actual substance partial image data indicating a predetermined first part (for example, cerebral gray matter) in the actual substance partial image data BPDk (74) (STEP 110).

The preprocessing unit 53*a* recognizes a first actual index value, which is the basic information used for diagnosis of disease for the test subject k, based on the first actual substance partial image data (STEP 112). As one example, the preprocessing unit 53*a* counts the number of image elements where the luminance value of each image element of the first actual substance partial image data has become equal to or higher than a predetermined value, and recognizes the number as the first actual index value. In place of or in addition to this, the preprocessing unit 53*a* may count the number of image elements where the luminance of each image element of the first actual substance partial image data is equal to or higher than a predetermined value, and recognize the number as the first actual index value. An image element whose luminance value is equal to or higher than the predetermined value indicates that the target substance (as examples, amyloid β protein or tau protein that are highly associated with Alzheimer's type dementia) is present at the corresponding part of the test subject k. The first actual index value indicating the number of these image elements indicates the extent of accumulation of the target substance at a predetermined first part.

Based on the part position data PDk, the preprocessing unit 53a recognizes second actual substance partial image data indicating a predetermined second part (for example, the cerebellum) in the actual substance partial image data BPDk (74) (STEP 114). The preprocessing unit 53a recognizes a second actual index value, which is an index of disease used as basic information for diagnosis of disease of the test subject k, based on the second actual substance partial image data (STEP 116). As one example, the preprocessing unit 53a counts the number of image elements in the second actual substance partial image data where the value indicating the luminance of each image element is a value indicating a predetermined luminance, and recognizes the number as the second actual index value. In place of or in addition to this, the preprocessing unit 53a counts the number of image elements where the luminance of each image element in the second actual substance partial image data is equal to or higher than a predetermined value, and recognizes the number as the second actual index value. In the same way as the first actual index value, the second actual index value indicates the degree of accumulation of the target substance at a predetermined second part.

The preprocessing unit 53a recognizes the actual index value Vk based on the first actual index value and the second actual index value and stores the actual index value Vk in the first storage unit 102 (STEP 118). As one example, the preprocessing unit 53a recognizes the ratio between the first actual index value and the second actual index value as the actual index value Vk.

When the processing in STEP 104 to STEP 118 has been executed for all of the subject data SDi in the training data set GDS and the subject data SDj in the test data set TDS, the present processing ends.

Figure 13:
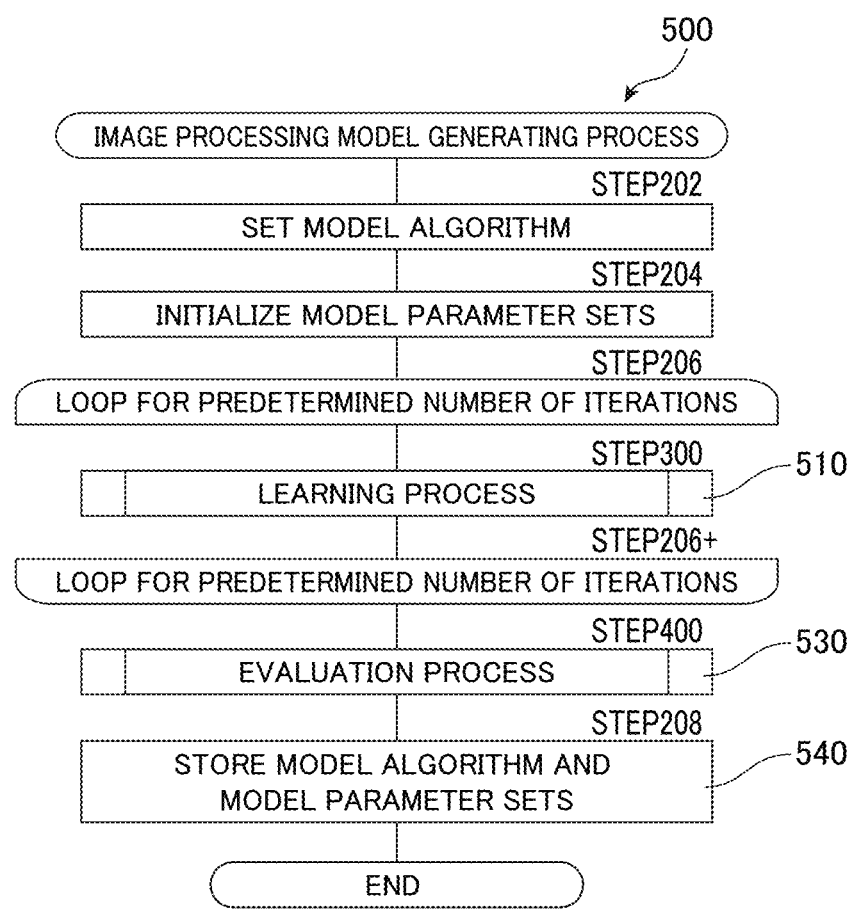
FIG. 13 is a flowchart depicting an overview of a generation process for an image processing model.

FIG. 13 depicts an overview of the image processing model generating process 500. The model generating unit 53b sets the model algorithm MA (61) (STEP 202). As one example, in accordance with the image processing model generating program MGP (50p), the model generating unit 53b loads the library to be used for machine learning and sets the number of layers of the multi-layer convolutional neural network to be realized by the library as the model algorithm 61, the functions to be used on the input layer, the hidden layer, and the output layer, the number of functions on each layer, and the like.

The model generating unit 53b initializes the model parameter set MP (62) (STEP 204). As one example, the model generating unit 53b sets a random value as each parameter. The model generating unit 53b loops a predetermined number of iterations (for example, 20,000 iterations) to execute the learning process 510 in STEP 300 (STEP 206). The model generating unit 53b executes an evaluation process 530 (STEP 400). The model generating unit 53b stores the model algorithm MA (61) and the model parameter set MP (62) in the first storage unit 102 (STEP 208). This completes the image processing model generating process.

Figure 14:
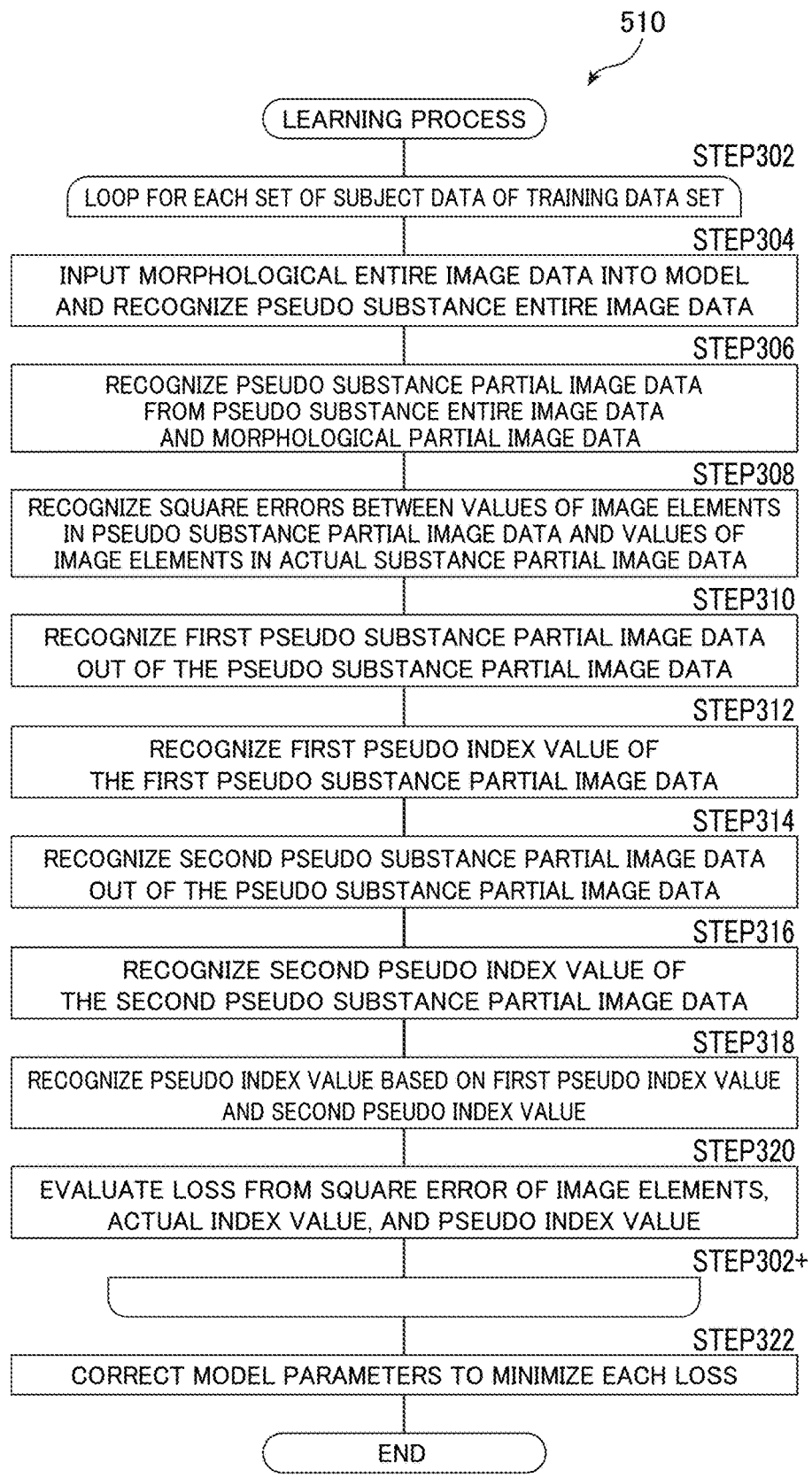
FIG. 14 is a flowchart depicting an overview of a learning process.

FIG. 14 depicts an overview of the learning process 510. The processing depicted in FIG. 14 is a model learning process in which the model algorithm MA is defined so as to use the morphological entire image data KDi (71), the blood analysis value BLi (91b), and the genotype GEi (91a) as inputs and to output pseudo substance entire image data predBDi corresponding to the actual substance entire image data BDi (72). The pseudo substance entire image data predBDi can be regarded as image data that models the distribution of a substance, for example, amyloid β protein or tau protein, related to a specific disease in the brain.

The model generating unit 53b executes the processing in STEP 302 to STEP 320 in a loop for each set of subject data SDI in the training data set 70 (STEP 302). The model generating unit 53b inputs the morphological entire image data KDi into the model and recognizes the outputted pseudo substance entire image data predBDi (STEP 304).

Figure 15:
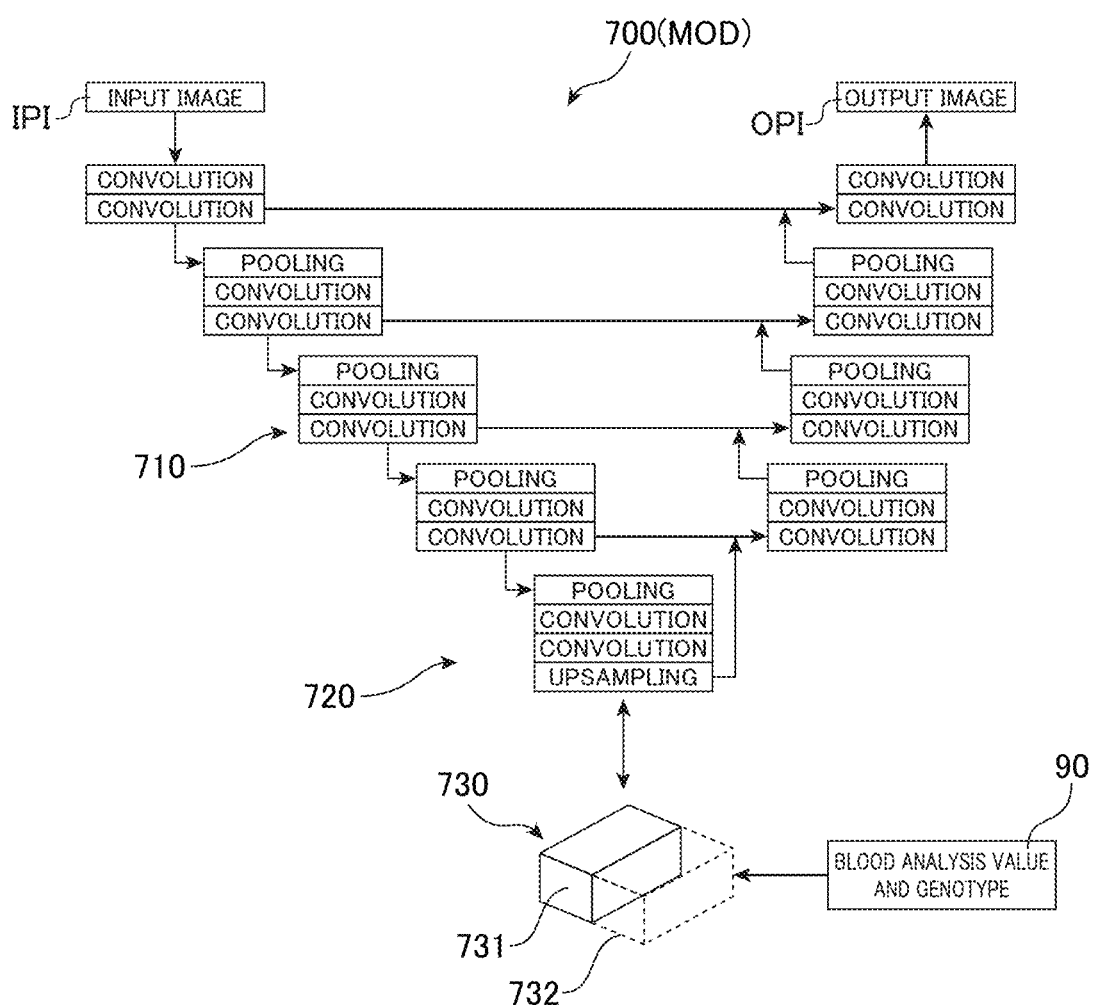
FIG. 15 is a diagram depicting an overview of U-NET.

A specific example of recognition of the pseudo substance entire image data predBDi will now be described with reference to FIG. 15. In the present embodiment, a recognition model MOD 700 with a U-net architecture, which is one example of a convolutional neural network architecture, is used to recognize the pseudo substance entire image data predBDi. A convolutional neural network structure with a U-Net architecture (or an autoencoder architecture where SkipConnection in the U-Net architecture is eliminated) performs optimization of internal parameters using multiple pairs of MR images that are inputs of the learning process 510 and corresponding (respective) actual PET images that have been actually captured. This U-net architecture model 700 is also effective as the model algorithm 61 of the image processing model 60 that generates the pseudo substance partial image data predBPDi (75) from the morphological entire image data KDi (71).

In the computation by the recognition model 700 that has the U-net architecture, three-dimensional morphology MR image data, which is the morphological entire image data KDi, is used as the input image data IPI. The input image data IPI is inputted into the hidden layer 710, and is pooled and convolved on each layer in the hidden layer 710 up to the feature layer 720. That is, in the recognition model 700, convolution and pooling are performed on the downward path. In the recognition model 700, convolution and up-sampling are performed on each layer from the feature layer 720 until obtaining the output image OPT, which is the result of the hidden layer 710. That is, in the recognition model 700, convolution and up-sampling are performed on the upward path, and in the present embodiment, the pseudo substance entire image data predBDi is restored (estimated) and recognized as the output image OPI. Note that the output of each layer on the downward path to the feature layer 720 of the hidden layer 710 into which the input image IPI is inputted is also inputted or transferred into a corresponding layer with the same depth on the upward path. That is, in the recognition model 700, the output of each layer on the downward path is merged with the input into the layer on the same depth on the upward path.

With the recognition model 700, it is possible to add the attribute information 90, which includes biomarkers, to the output data from the feature layer 720. In more detail, feature data (L×M×(N+r)×1) 730, produced by combining image feature data (3D format: L×M×N×1) 731, which is the output of the immediately preceding layer of the feature layer 720 on the downward path, and data (data with r features: L×M×r×1) 732 including values determined by the blood analysis value BLi (91b) and/or the genotype GEi (80a) for example, out of the attribute information 90 including the biomarker information, is inputted into the feature layer 720.

In this way, in the recognition model 700, the data 730 outputted from the feature layer 720 is combined with data on biomarkers highly related to Alzheimer's type dementia as the specific disease, and in particular biomarkers closely related to an accumulation tendency of amyloid β protein or tau protein in the brain, which makes it possible to improve the reproducibility of the image data estimated by the recognition model 700.

Note that as the biomarkers, other biomarkers highly related to Alzheimer's type dementia, such as the educational history of the subject, may be used. Although it is assumed in the above description that the output data 731 from the feature layer 720 has been combined with the biomarker-based data 732, which is a value or values based on the biomarkers and includes a value or values determined by the blood analysis value BLi and the genotype GEi, it is also possible to combine data 732 based on biomarkers with an input at another position, in more detail, into any layer of the hidden layer 710. The data 732 based on the same biomarkers may be combined multiple times with any layer. In addition, when using sets of data 732 based on a plurality of biomarkers, each set of data based on respective biomarkers 732 may be combined with inputs into respectively different layers.

The model generating unit 53b recognizes the pseudo substance partial image data predBDi by extracting the partial image data corresponding to the morphological partial image data KBDi from the pseudo substance entire image data predBDi (STEP 306). The model generating unit 53b calculates, for each value of an image element predBDi (x,y,z) in the pseudo substance partial image data predBDi, the square of the error relative to the value of the image element BDi (x,y,z) in the actual substance partial image data BDi with the same coordinates (x,y,z) to find an average value MSEi of the square error for the pseudo substance partial image data predBDi (STEP 308). The model generating unit 53b recognizes, based on the part position data PDi, first pseudo substance partial image data indicating a predetermined first part (for example, cerebral gray matter) out of the pseudo substance partial image data predBPDi (75) (STEP 310).

The model generating unit 53b recognizes a first pseudo index value, which is basic information for the diagnosis of disease for the test subject i, based on the first pseudo substance partial image data (STEP 312). As one example, the model generating unit 53b counts the number of image elements for which a value indicating luminance of each image element in the first pseudo substance partial image data is a value indicating a predetermined luminance, and recognizes the count value as the first pseudo index value. In place of or in addition to this, the preprocessing unit 53a may count the number of image elements in the first pseudo substance partial image data where the luminance of the image element is equal to or higher than a predetermined value and recognize the count number as the first pseudo index value.

The model generating unit 53b recognizes, based on the part position data PDi, the second pseudo-substance partial image data indicating a predetermined second part (for example, the cerebellum) out of the pseudo-substance partial image data predBPDi (STEP 314). The model generating unit 53b recognizes the second pseudo index value, which is the index of disease used as basic information for the diagnosis of disease in the test subject i, based on the second pseudo substance partial image data (STEP 316). As one example, the model generating unit 53b counts the number of image elements where the luminance value of the image element is equal to or higher than a predetermined value out of the second pseudo substance partial image data, and recognizes the count number as a second pseudo index value. The model generating unit 53b recognizes a pseudo index value PredVi based on the first pseudo index value and the second pseudo index value and stores the pseudo index value PredVi in the first storage unit 120 (STEP 318). As one example, the model generating unit 112 recognizes the ratio of the first pseudo index value to the second pseudo index value as the pseudo index value predVi. The pseudo index value predVi corresponds to the actual index value Vi relating to a specific disease. Note that as described above, the actual index value Vi is an index value for determining whether the subject is at risk of developing a certain disease. In the present embodiment, the pseudo index value predVi is an index value for determining whether the test subject i is at risk of developing a certain disease, as one example, Alzheimer's type dementia. As one example, when the actual index value Vi is an actual SUVR, it can be said that the pseudo index value predVi is a pseudo SUVR.

The model generating unit 53b evaluates the loss Ei with respect to the subject data SDi of the present model based on indices that measure the differences between voxel elements, as examples, the square error MSEi for image elements, the actual index value Vi, and the pseudo index value predVi (STEP 320). The model generating unit 53b evaluates the loss Ei with respect to the subject data SDi of the present model using Equation (2) given earlier.

After the loop processing of STEP 302 has ended, the model generating unit 53b modifies the model parameter set MP using an error back propagation method or the like so that each loss Ei is minimized (STEP 322). This completes the present processing.

Figure 16:
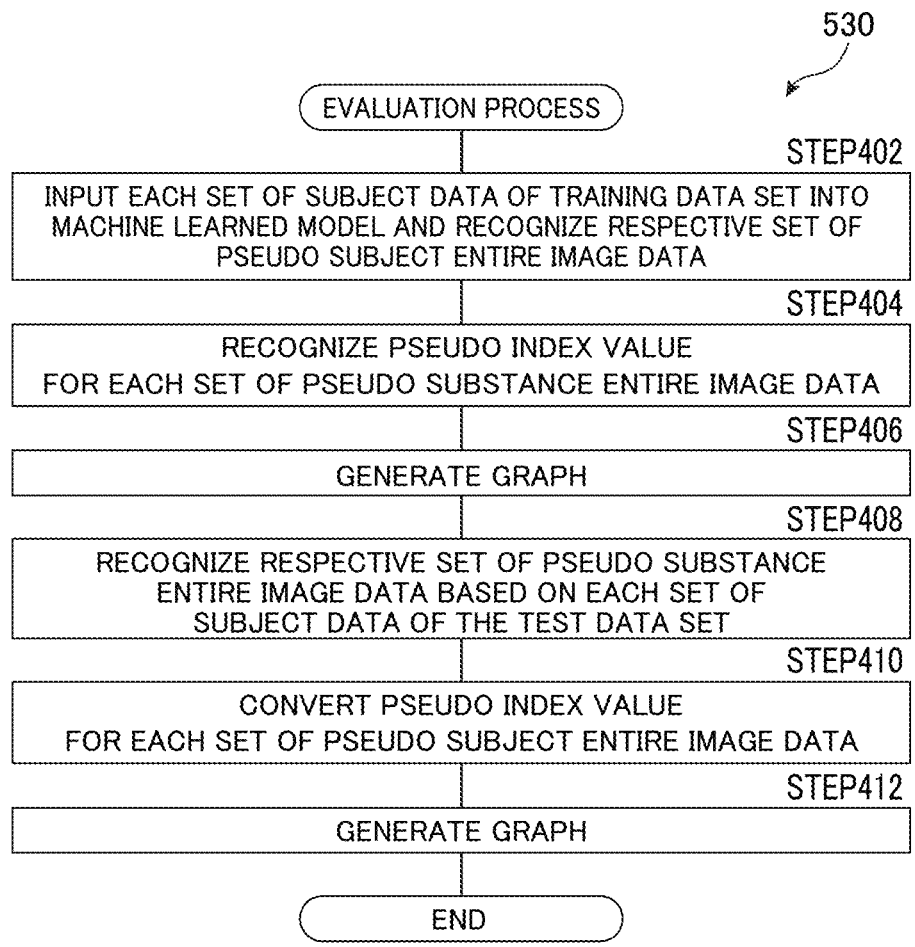
FIG. 16 is a flowchart depicting an overview of an evaluation process.

The model generating unit 53b performs evaluation process 530 depicted in overview in FIG. 16. The model generating unit 53b inputs each set of subject data SDi of the training data set GDS (70) into the machine learned model 60 and performs recognition on respective set of pseudo substance entire image data predBDi that has been outputted (STEP 402). The model generating unit 53b recognizes each set of pseudo index value predVi for the respective set of pseudo substance entire image data predBDi via the same processing as STEP 306 and STEP 310 to STEP 318 of the learning process 510 (STEP 404). The model generating unit 53b generates a two-dimensional coordinate graph with the actual index value Vi as the horizontal axis and the pseudo index value predVi as the vertical axis, as one example, the graph depicted in FIG. 4 (STEP 406).

The model generating unit 53b inputs each set of subject data SDj of the test data set TDS (79) into the machine learned model 60 and performs recognition on each set of pseudo substance entire image data predBDj that has been outputted (STEP 408). The model generating unit 53b recognizes respective pseudo index value predVj for each set of the pseudo substance entire image data predBDj via the same processing as STEP 306 and STEP 310 to STEP 318 of the learning process 510 (STEP 410). The model generating unit 53b generates a two-dimensional coordinate graph that has the actual index value Vj as the horizontal axis and the pseudo index value predVj as the vertical axis, as one example, FIG. 5 (STEP 412). Correlations between each pseudo-index value predVj recognized from respective set of pseudo substance entire image data predBDj in the test data set TDS and correlations between each pseudo-index value predVi recognized from respective set of pseudo substance entire data predBDj in the training data set GDS are compared to confirm the performance of the model 60.

Figure 17:
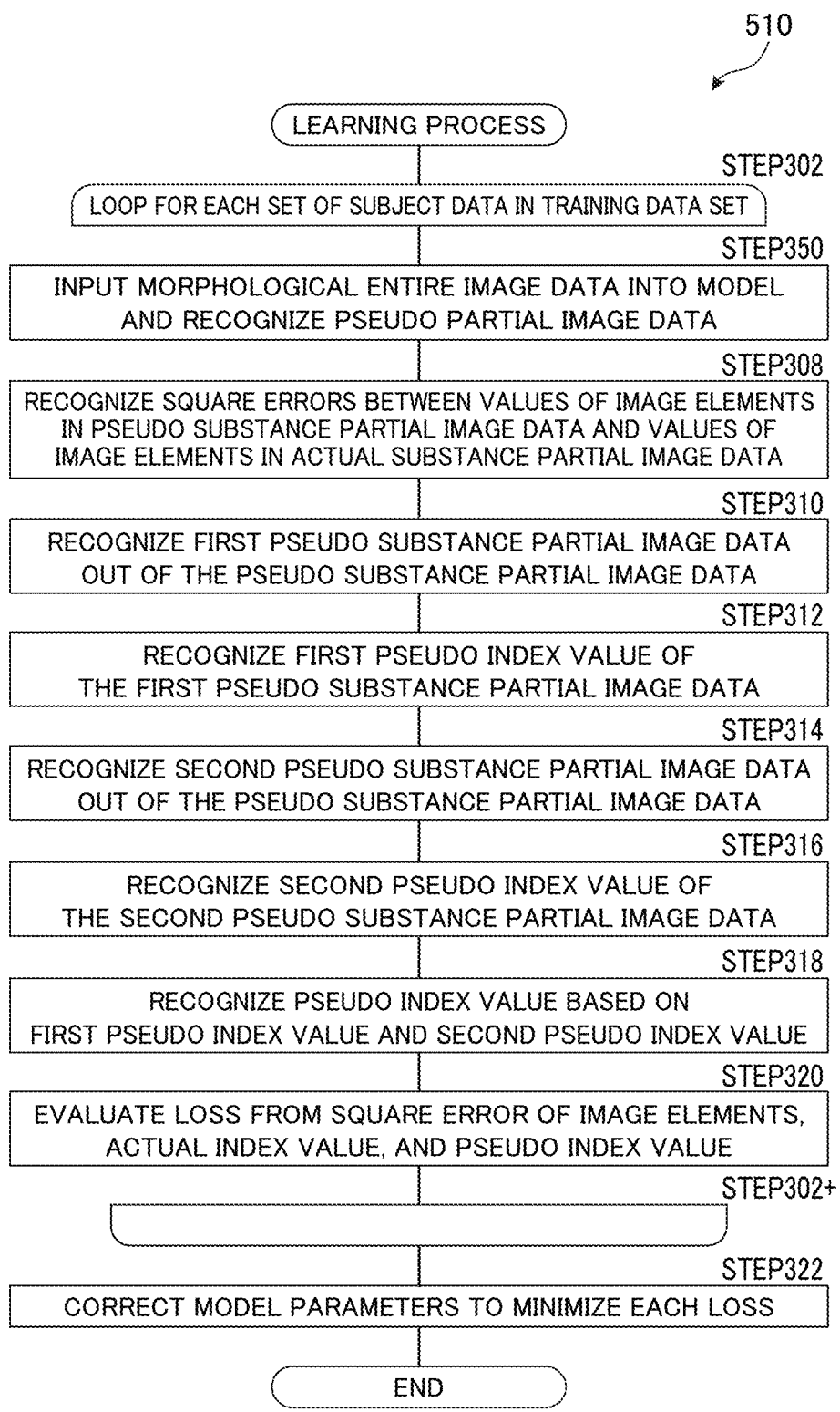
FIG. 17 is a flowchart depicting an overview of another learning process.

FIG. 17 depicts a different example of the learning process 510. The learning process 510 in FIG. 14 is a learning process for a model in which the model algorithm MA is defined so as to input the morphological entire image data KDi (71) and output the pseudo substance entire image data predBDi corresponding to the actual substance entire image data BDi. The learning process 510 depicted in FIG. 17 trains the model 60 in which the model algorithm MA

(61) is defined so as to, based on the morphological entire image data KDi (71) as an input, output the pseudo substance partial image data predBPDi (75) corresponding to the actual substance partial image data BPDi (74) depicted in FIG. 2.

This processing differs to the learning process depicted in FIG. 14 in that the model generating unit 53b executes STEP 350 in place of STEP 304 to STEP 306, but is otherwise the same. In STEP 350, the model generating unit 53b inputs the morphological entire image data KDi into the model and recognizes the outputted pseudo substance partial image data predBPDi+. In STEP 308 onwards, the model generating unit 53b performs processing using the pseudo substance partial image data predBPDi+ recognized in STEP 350.

Figure 18:
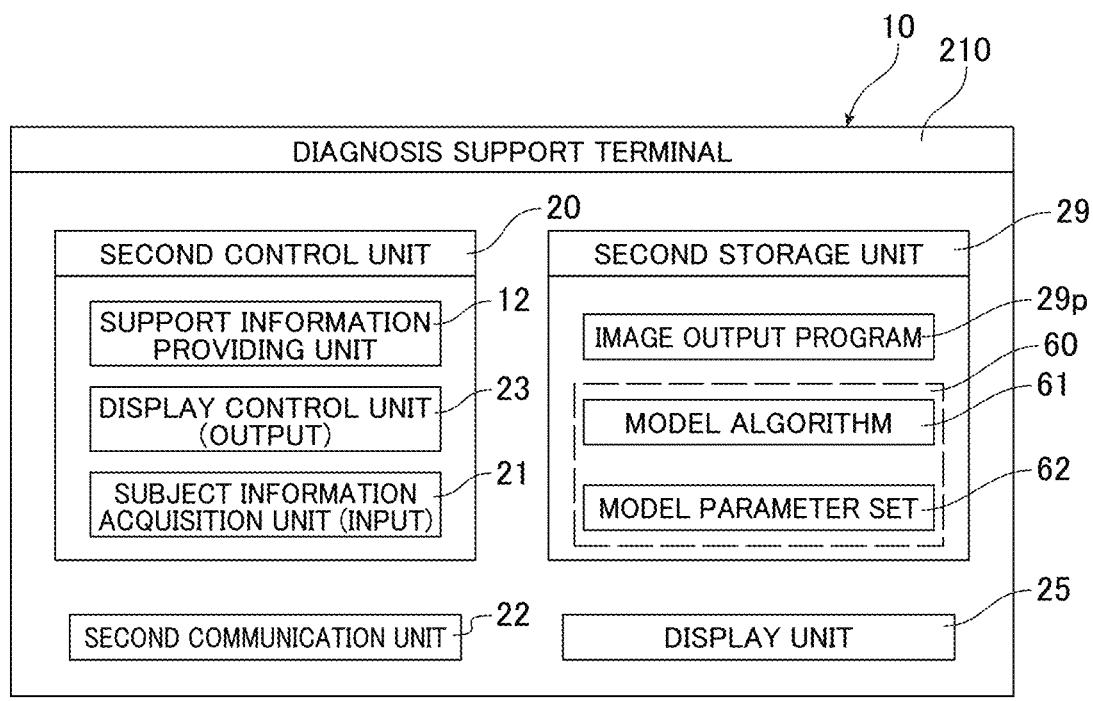
FIG. 18 is a block diagram depicting an overview of a diagnosis support terminal.

FIG. 18 further depicts the configuration of a terminal (diagnosis support terminal or image display apparatus) 210 of the medical institution 200. The support terminal 210 may be composed of a desktop computer, a laptop computer, a tablet terminal, a smartphone, or the like. The support terminal 210 includes a second control unit 20, a second storage unit 29, a second communication unit 22, and a display unit 25. The second control unit 20 is configured, for example, with a computational processing apparatus such as a CPU (Central Processing Unit), a cache memory, an I/O device, and the like. The second control unit 20 reads out and executes an image output program 29p stored in the second storage unit 29, and thereby functions as the diagnosis support information providing unit (information providing device, information provision module or display data recognition unit) 12, the display control unit (output unit) 23, and the subject information acquiring unit (input unit) 21. In this example, the second control unit 20 functions as a stand-alone diagnosis support module 10.

As one example, the second storage unit 29 may include a main storage device, such as a memory, and an auxiliary storage device, such as an HDD. The second storage unit 29 is configured to store the image output program 29p and the machine learned (trained) image processing model 60, which includes the model algorithm 61 and the model parameter set 62. The machine learned image processing model 60 may be downloaded via communication from the model providing module 50. Alternatively, the image processing model 60 may be loaded from a portable storage medium such as a CD, a DVD, or a USB memory.

The second communication unit 22 is configured to be capable of communicating, via a network using wired or wireless communication, with each of the model providing module 50, the morphological image capturing apparatus 221, and other external devices. As one example, the display unit 25 may include a liquid crystal panel. The display unit 25 is configured to display an image in response to a signal from the display control unit 23.

Figure 19:
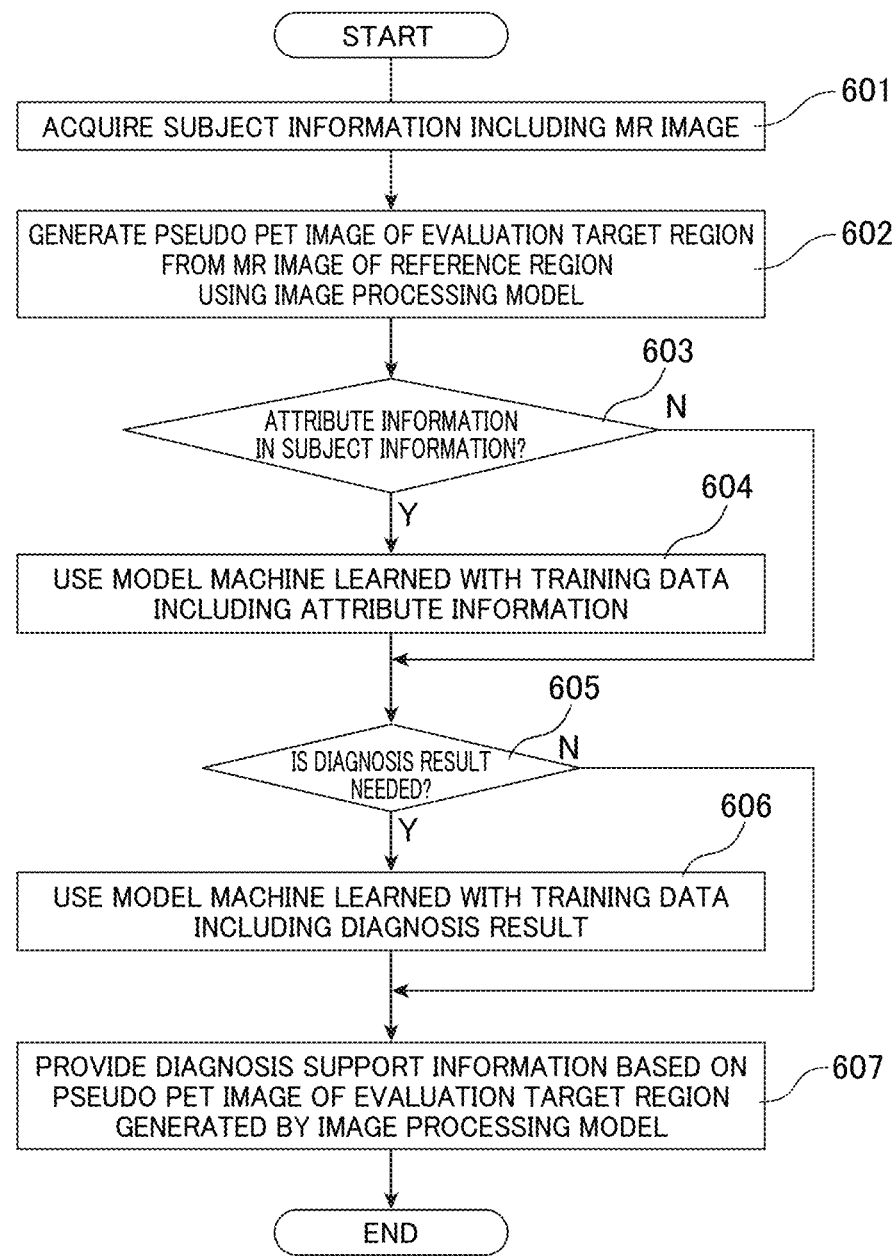
FIG. 19 is a flowchart depicting an overview of processing that provides diagnosis support information.

FIG. 19 depicts an overview of the processing in the diagnosis support module 10. In step 601, the subject information acquiring unit (patient information acquisition interface) 11 of the diagnosis support module 10, or the input interface 21 that functions as an acquisition unit acquires the subject information (patient information) 105 including an MR image 15 of the brain of the target subject 5. The MR image 15 is one example of actual first type image data (actual Type-1 image data) that mainly includes information on morphology and is acquired with the brain including the evaluation target region 82 as the reference region 81, and the MR image 15 included in the subject information 105 is one example of individual actual image data of the target subject 5 including at least the reference region 81. Note that although an example where diagnosis support is provided using a pseudo PET image generated from an MR image with Alzheimer's disease of the subject 5 as the target will be described below, as described earlier, it is also possible to provide a diagnosis support service that uses the image processing model 60 in the same way for other symptoms and other types of image.

In step 602, the information providing unit 12 generates the PET image 115 including the five parts of the evaluation target region 82 from the MR image 15 of the entire brain (reference region) 81 included in the subject information 105 by the image processing model 60 that has been machine learned to generate a pseudo PET image 75, which is pseudo second type image data (pseudo Type-2 image data) of the evaluation target region 82, from the MR image 71, which is actual first type image data (actual Type-1 image data) of the reference region 81 based on the training data 70.

The actual Type-2 image data included in the training data 70 for machine learning of the image processing model 60 are PET images 72 of the actual substance image data which includes distribution information visualizing the abnormality to be diagnosed, in this example, the distribution of amyloid β which is the first substance related to Alzheimer's disease. The image processing model 60 is a model including parameters 62 that have been provided (learned, trained) so as to reduce the difference between the actual index value and the pseudo index value, using the loss function Ei including the actual index value Vi (SUVR), which is obtained from the distribution information of the first substance in the evaluation target region 82 of the actual Type-2 image data, and the pseudo index value predVi (predSUVR), which is obtained from the pseudo distribution information corresponding to the distribution of the first substance included in the pseudo Type-2 image data of the evaluation target region 82. The loss function Ei also includes a degree of deviation, for example, MEEi, indicating the extent of deviation of the values of the voxel elements (image elements) of the pseudo Type-2 image data (pseudo PET image) 75 of the evaluation target region 82 from the values of image elements in the actual Type-2 image data (PET image) 74 of the evaluation target region 82.

When, in step 603, the subject information 105 obtained in step 601 includes attribute information 14 including the biomarkers 91 of the target subject 5, in step 604, the image processing model 60, which includes the parameter set 62 that has been obtained in the machine learning based on the training data 70 with the attribute information 90 including information 91 related to biomarkers of the plurality of test subjects, is used to generate the pseudo PET image 115.

If, in step 605, diagnosis support information 110 that includes a diagnosis result (pseudo-diagnosis result or estimated diagnosis result) 117 is requested, an image processing model 60 including a parameter set 62 that has been obtained in the machine learning based on the training data 70 including diagnosis results 94 of the abnormality that is the diagnosis target for a plurality of test subjects is used in step 606. In step 607, the diagnosis support information 110 based on the pseudo PET image 115 of the evaluation target region 82 generated by the image processing model 60 is provided based on the data included in the subject information 105. The diagnosis support information 110 may include a pseudo index value 116 and a pseudo diagnosis result 117 in addition to the pseudo PET image 115. The pseudo index value 116 and/or the pseudo diagnosis result 117 may be included in the diagnosis support information 110 in place of the pseudo PET image 115.

By outputting the diagnosis support information 110 provided by the diagnosis support module 10 or the diagnosis support information providing unit 12 to the image display terminal 25, the terminal 210 of the medical institution 200 supports, helps or assists diagnosis by medical personnel, such as a doctor 8. The output method of the diagnosis support information 110 can be set in various ways. The pseudo PET image 115 included in the diagnosis support information 110 may be displayed separately or may be displayed alongside or superimposed on the MR image 15 of the target subject 5.

As one example, in addition to the MR image 15 based on the morphological entire image data, one or both of the pseudo PET image 115 based on the pseudo substance partial image data and the pseudo index value 116 indicating an index value of disease for the target subject 5 is displayed, thereby providing the doctor 8 with useful information for diagnosing the presence, absence, or risk of disease for the target subject (patient) 5. In particular, by displaying both the pseudo PET image 115 based on the pseudo substance partial image data and the pseudo index value 116 indicating the index value of disease for the target subject 5, it becomes easier for the doctor 8 to more fully recognize the state of the target subject 5.

As described above, in the diagnosis support system and method with the image processing model (image output model) 60, by using a 3D image, such as an MR image or a CT image which place a relatively small burden on the target subject or the patient, that mainly acquires information on morphology, although limited to various areas of interest (ROI, evaluation target regions) 82, it is possible to accurately generate 3D images of substances related to various abnormalities (diseases) and to provide the diagnosis support information 110 based on this. Accordingly, it is possible to obtain information which is comparable to PET images and the like at a high frequency without placing a burden on the subject or patient, and to provide information on prevention, progression or diagnosis of abnormalities (diseases) in a timely manner. This means that the diagnosis support system can be applied not only to the diagnosis of diseases but also to applications such as selection of clinical trial subjects for drug and/or medicine development and clinical monitoring. The diagnosis support system is also not limited to diagnosis of living bodies including humans and livestock, but is also useful in applications such as non-destructive diagnosis of the internal state of structures for which diagnostic imaging is effective.

Although morphological entire image data is inputted into the model in the embodiment described above, it is possible to use a configuration where the morphological partial image data is inputted into the model instead of or in addition to this. In the embodiment described above, an example in which the morphological partial image data KPDi and the actual substance partial image data BPDi are used as the image data in the learning process is described. However, only the morphological entire image data KDi and the actual substance entire image data BDi may be used as image data in the learning process. Also, although the morphological partial image data and the pseudo substance partial image data are outputted as the image data in the image display processing in the embodiment described above, it is also possible to output the pseudo substance entire image data in place of the pseudo substance partial image data. Also, in the above embodiment, a case where a model with a U-net architecture is used as the recognition model 700 has been described. However, as the recognition model 700, a model with a different neural network architecture, such as Auto Encoder, may be used.

One of the aspects described above is a display method executed by a computer equipped with a display unit. The display method includes: a subject morphology image recognition step that recognizes morphology entire image data in which morphology inside the body of the subject has been captured; a subject pseudo substance image part recognition step that inputs morphological image data, which includes image portions of the morphology entire image data of the patient, into an image output model generated by a generating method for the image output model and recognizes pseudo substance image data that pseudo-indicates a distribution of a target substance in one part inside the body of the patient outputted from the image output model; and a display step that outputs the pseudo substance image data, which has been recognized in the subject pseudo substance image part recognition step, to the display unit.

The display method may include a pseudo index value recognition step that recognizes a pseudo index value related to a disease of the subject based on the pseudo substance image data, and the display step may include outputting the pseudo substance image data recognized in the subject pseudo substance image part recognition step and the pseudo index value recognized in the pseudo index value recognition step to the display unit. Note that in this specification, one device "recognizing" information refers to when any type of computational processing for acquiring the information is executed, such as the device receiving the information from another device, the device loading the information stored on a storage medium connected to the device, the device acquiring the information based on a signal outputted from a sensor connected to the device, the device deriving the information by executing predetermined computational processing (calculation processing, search processing, or the like) based on received information, information stored on a storage medium, or information acquired from a sensor, the device receiving the information, which is the result of computational processing by another device, from the other device, and the device reading the information from an internal storage device or an external storage device according to a received signal.

Another aspect of the above is an image display method executed by a computer equipped with a display unit. This image display method includes: a subject morphology image recognition step that recognizes morphology image data where morphology inside the brain of the subject has been captured; a subject biomarker recognition step that recognizes a biomarker associated with a specific disease of the subject; a pseudo substance image recognition step that inputs morphological image data of the subject and values based on the biomarkers into an image output model to recognize pseudo substance image data that models a distribution of a target substance associated with the specific disease in the brain of the subject outputted from the image output model; and a display step that outputs the pseudo substance image data recognized in the pseudo substance image recognition step or a pseudo index value, which is recognized based on the pseudo substance image data and is a value related to the occurrence of the specific disease of the subject, to the display unit.

According to an image display method with this configuration, in the pseudo substance image recognition step that acquires the pseudo substance image data to be used when diagnosing a specific disease, the pseudo substance image data that models the distribution of the target substance in the brain of the subject is recognized by inputting a value based on a biomarker related to the specific disease of the subject in addition to the morphological image data of the subject's brain. In this way, when recognizing the pseudo substance image data, by generating the pseudo substance image data so as to reflect a value based on a biomarker related to the specific disease of the subject, it is possible to improve the estimation accuracy of the distribution of a target substance related to a specific disease in the brain compared to when the distribution of the target substance is estimated based on only morphological image data, and in turn to improve the reproduction accuracy of the pseudo substance image data and its pseudo index value.

By improving the estimation accuracy of the distribution of the target substance related to a specific disease in the brain, it is possible to provide more useful information for diagnosis of brain disease and the like. In addition, it is possible to construct a model, such as a neural network, that discriminates between diseases using a large number of images containing information on target substances related to specific diseases in the brain. When doing so, instead of preparing a large number of substance images that are typically very costly, pseudo substance images with high reproduction accuracy can be used as a substitute.

The image output model may have a U-net architecture. The pseudo substance image recognition step may include adding a value based on a biomarker in the input layer of the U-net architecture. The pseudo substance image recognition step may include adding a value based on a biomarker in the feature layer of the U-net architecture. The value based on the biomarker may include a value obtained by analyzing the blood of the subject or may include a value based on the genotype of the subject. The morphological image data may be CT image data or MR image data indicating the morphology of the entire brain of the subject that has been captured in cross-section.

According to this image display method, by inputting the morphological image data of the brain on the input layer of the U-net architecture and inputting a value based on a biomarker related to a specific disease on the input layer or the feature layer, it is possible to further improve estimation accuracy for the distribution of the target substance related to the specific disease inside the brain, and in turn to further improve the reproduction accuracy of the pseudo substance image data and its pseudo index value. According to this image display method, as one example, by using values and gene types obtained by analyzing blood, which are biomarkers related to the distribution of (highly relevant) amyloid β protein or tau protein in the brain, when determining whether there is a risk of developing Alzheimer's type dementia, it is possible to make a highly accurate diagnosis of Alzheimer's type dementia as the specific disease.

Another aspect described above is an image display device including: a display unit; a display data recognition unit that recognizes the morphological entire image data in which the morphology of the subject's body is captured and inputs morphological image data including an image portion of the morphological entire image data of the subject into an image output model generated by a generation method for an image output model, to recognize pseudo substance image data that pseudo-indicates the distribution of the target substance at one part of the body of the subject outputted from the image output model; and a display control unit that outputs the pseudo substance image data recognized by the display data recognition unit to the display unit. The display data recognition unit may recognize the pseudo substance image data and a pseudo index value related to a disease of the subject. The display control unit may output the pseudo substance image data and the pseudo index value to the display unit.

Another aspect described above is an image display device. The image display device includes: a display unit; a display data recognition unit that recognizes morphological image data in which the morphology of the subject's brain is captured, recognizes a value based on a biomarker relating to a specific disease of the subject, recognizes, by inputting the morphological image data of the subject and the value based on the biomarker into an image output model, pseudo substance image data that models a distribution of a target substance relating to a specific disease in the brain of the subject outputted from the image output model, and recognizes a pseudo index value that is a value relating to occurrence of the specific disease of the subject and is recognized based on the pseudo substance image data; and a display control unit that outputs the pseudo substance image data recognized by the display data recognition unit, the pseudo index value, or both to the display unit Another aspect described above is a method of generating an image output model. The generation method is a method executed by a computer equipped with a storage unit storing morphological image data, which is a captured image of the morphology of the subject's brain, actual substance image data indicating the distribution of the target substance related to the specific disease of the subject in the subject's brain, and a value based on a biomarker associated with the specific disease of the subject, and the method includes a step of inputting the morphological image data and the value based on a biomarker and correcting a model that outputs pseudo substance image data, which is an image relating to the distribution of the target substance in the brain of the subject, based on the actual substance image data.

According to the method of generating the image output model of the above, in the model generating step, the model that acquires the morphological image data of the subject's brain and the value based on the biomarker related to the specific disease of the subject stored in the storage unit outputs the pseudo substance image data regarding the distribution of the target substance related to the specific disease at one part of the subject is corrected based on the actual substance partial image data regarding the distribution of the target substance in the subject's brain. By doing so, an image output model is generated. By acquiring a value based on a biomarker related to the specific disease of the subject in addition to morphological image data on the subject's brain, compared to when only morphological data of the subject's brain is inputted, it is possible to improve the accuracy with which the image output model estimates the distribution of the target substance related to the specific disease in the subject's brain. By improving the estimation accuracy for the distribution of the target substance in the brain, it is possible in turn to provide more useful information for the diagnosis of diseases and the like.

The storage unit may store morphological partial image data including an image portion of one part of the morphological image of the subject and actual substance partial image data produced by extracting an image portion relating to the distribution of the target substance in the one part of the actual substance image of the subject. The model generating step may include a step of correcting a model, which acquires the morphological partial image data and the value based on a biomarker and outputs pseudo substance image data including an image portion relating to the distribution of the target substance in one part of the subject's brain, based on the actual substance partial image data.

The generation method is a method executed by a computer equipped with a storage unit storing morphological image data, which includes an image portion relating to one part of the morphological entire image data which is a captured image of the morphology of one or a plurality of parts of the subject's body, and actual substance partial image data obtained by extracting an image portion relating to the distribution of the target substance in the one part out of the one or a plurality of parts of the subject in the actual substance entire image data indicating the distribution of the target substance in the body of the subject, and the method may include a model generating step that generates the image output model by inputting the morphological image data and correcting a model that outputs the pseudo substance image data including an image portion relating to the distribution of the target substance at the one part of the subject's body based on the actual substance partial image data.

According to the method of generating an image output model above, in the model generating step, the model that acquires the morphological image data stored in the storage unit and outputs pseudo-substance image data regarding the distribution of the target substance related to the specific disease at the part of the subject, for example, one part of the brain, is corrected based on the actual substance partial image data relating to the distribution of the target substance in that part of the subject (that is, part of the brain). By doing so, the image output model is generated. When diagnosing a disease or the like, for example, brain disease, what is important is not the distribution of the target substance related to the disease in the body, for example, the brain as a whole, but the distribution within a partial region, and for this reason, compared to a case where the model is corrected based on only actual substance entire image data, the accuracy with which the image output model estimates the distribution of the target substance in that part of the subject can be improved. By improving the estimation accuracy of the distribution of the target substance in that part (here, a part of the brain), it is possible in turn to provide more useful information for diagnosis of disease and the like.

This method of generating an image output model may include an actual index value recognizing step of recognizing an actual index value regarding the specific disease of the subject based on the actual substance partial image data, and the model generating step may include: a degree of deviation evaluating step of evaluating a degree of deviation indicating the extent of deviation of a value of an image element in the pseudo substance image data from the value of an image element in the actual substance partial image data; a pseudo index value recognizing step of recognizing a pseudo index value relating to the disease of the subject based on the pseudo substance image data; and a correcting step of correcting the model based on the degree of deviation, the actual index value, and the pseudo index value.

According to this method of generating the image output model, in the model generating step, the degree of deviation, which indicates the extent of deviation of image elements in the pseudo substance image data from image elements in the actual substance partial image data is evaluated. Based on the pseudo substance image data, a pseudo index value relating to the disease of the subject is then recognized. After this, the model is corrected based on the degree of deviation, the actual index value, and the pseudo index value. By doing so, the model is corrected by taking into account both image elements and an index value for disease. As a result, it is possible to make the image elements in the data outputted from the image output model and the index value related to the disease closer to actual data, and in turn to provide more useful information for the diagnosis of disease or the like.

The actual index value recognizing step may include a step of recognizing a first actual index value based on the distribution of the target substance at a first part of the subject included in the actual substance partial image data and recognizing a second actual index value based on a distribution of the target substance at a second part of the subject included in the actual substance partial image data. The pseudo index value recognizing step may include a step of recognizing a first pseudo index value based on the distribution of the target substance at a first part of the subject included in the pseudo substance partial image data and recognizing a second pseudo index value based on a distribution of the target substance at a second part of the subject included in the pseudo substance partial image data. The correcting step may include correcting the model based on the degree of deviation, the first actual index value, the second actual index value, the first pseudo index value, and the second pseudo index value.

For some brain diseases, the diagnosis may change depending not only on the total amount of the target substance in the brain but also on which parts and how the target substance related to the specific disease is distributed in the brain. According to the method of generating an image output model above, the model is corrected by taking into account index values for each of the plurality of parts of the brain of the subject. By doing so, it is possible to make the information provided for diagnosis of diseases and the like more useful.

The method of generating the image output model may include a position recognizing step of recognizing the position of the first part and the position of the second part in the morphology entire image data or the actual substance entire image data. The pseudo index value recognizing step may include a step of recognizing a position of the first part and a position of the second part in the pseudo substance image data based on the position of the first part and the position of the second part in the morphological entire image data or the actual substance entire image data, recognizing the first pseudo index value based on the distribution of the target substance at the position of the first part in the pseudo substance image data, and recognizing the second pseudo index value based on the distribution of the target substance at the position of the second part in the pseudo substance image data.

Since the position or size of a part in the human brain varies between people, at the time when an image is generated, it is unclear which parts are located where in the image from the generated image itself. In view of this, according to the method of generating the image output model, the position of the first part and the position of the second part in the pseudo substance image data are recognized based on the position of the first part and the position of the second part in the morphological image data or the actual substance image data. By doing so, it is unnecessary to perform analysis into what data a part included in the pseudo substance image data corresponds to and the like, so that the calculation cost when generating the image output model can be reduced.

In this method of generating an image output model, the morphological image data may be CT image data or MR image data indicating the morphology of the entire brain of the subject that has been captured in cross-section, and the actual substance partial image data may be image data of a PET image relating to the cerebral gray matter and the cerebellum in the brain of the subject. The model generating step may include a step of generating an image output model by correcting a model, which inputs CT partial image data or MRI partial image data including an image portion related to the cerebral gray matter and the cerebellum in CT image data or MR image data stored in the storage unit and outputs pseudo PET image data including an image portion relating to the distribution of amyloid β protein or tau protein in the cerebral gray matter and the cerebellum of the subject, based on the image data of the PET image.

According to the method of generating an image output model above, an image output model is generated by correcting a model, which acquires CT partial image data or MRI partial image data including an image portion related to cerebral gray matter and the cerebellum in the CT image data or MR image data stored in the storage unit and outputs pseudo PET image data including an image portion relating to the distribution of amyloid β protein or tau protein in the cerebral gray matter and the cerebellum of the subject, based on partial image data of the PET image. The distribution of amyloid β protein or tau protein in cerebellar gray matter and the cerebellum can be used as basic information for determining the risk of dementia in particular, and for this reason an image output model that estimates the distribution of amyloid β protein or tau protein in cerebral gray matter and the cerebellum is generated. By providing entire image data outputted from this image output model to a doctor or the like, it is possible to improve the usefulness of basic information in determining the risk of dementia.

Note that the information such as images, medical cases (example diseases), and index values disclosed above are mere examples, and the present invention is not limited to the description and illustrations thereof. In addition, although the specific embodiments of the present invention have been described above with reference to the drawings, various other embodiments and modifications can be conceived by those of skill in the art without departing from the scope and spirit of the invention. Such other embodiments and modifications fall within the range of the following patent claims which defines the present invention.

The invention claimed is:

1. A system comprising:
an acquisition unit that acquires a set of individual actual first type image data including at least a reference region, which includes an evaluation target region as a part, of a target subject; and
an information providing unit that provides diagnosis support information based on a set of pseudo second type image data of the evaluation target region generated from the set of the individual actual first type image data of the target subject by an image processing model machine learned with training data that includes sets of actual first type image data of reference regions of a plurality of test subjects and sets of actual second type image data including evaluation target regions of the plurality of test subjects, so as to generate a set of the pseudo second type image data limited to the evaluation target region from a set of the actual first type image data of the reference region.

2. The system according to claim 1,
wherein the image processing model is a model including a parameter obtained by learning with a loss function that includes a degree of deviation indicating an extent of deviation of values of image elements in pseudo second type image data of the evaluation target region from values of image elements in actual second type image data of the evaluation target region.

3. The system according to claim 1,
wherein the actual second type image data is actual substance image data including distribution information visualizing a distribution of a first substance related to an abnormality to be diagnosed, and
the image processing model is a model including a parameter obtained by learning, using a loss function including an actual index value obtained from distribution information of the first substance in the evaluation target region of the actual second type image data and a pseudo index value obtained from pseudo distribution information that corresponds to a distribution of the first substance and is included in the pseudo second type image data of the evaluation target region, so that a difference between the actual index value and the pseudo index value is reduced.

4. The system according to claim 3,
wherein the loss function includes a degree of deviation indicating an extent of deviation of values of image elements in the pseudo second image data of the evaluation target region from values of image elements in actual second type image data of the evaluation target region.

5. The system according to claim 3,
wherein the evaluation target region includes a plurality of parts, the actual index value is calculated from distribution information of the plurality of parts, and the pseudo index value is calculated from a set of pseudo distribution information of the plurality of parts.

6. The system according to claim 3,
wherein the information providing unit provides diagnosis support information including a pseudo index value obtained from the pseudo second type image data of the evaluation target region generated from the individual actual first type image data of the target subject.

7. The system according to claim 3,
wherein the actual first type image data includes CT image data or MR image data that covers a brain as the reference region, and the actual second type image data includes PET image data, and
the pseudo index value includes a pseudo SUVR value.

8. The system according to claim 3,
wherein the actual first type image data includes CT image data or MR image data that covers a brain as the reference region, and the actual second type image data includes SPECT image data, and
the pseudo index value includes a pseudo BR value.

9. The system according to claim 3,
wherein the training data includes diagnosis results of the abnormality to be diagnosed for the plurality of test subjects, and
the information providing unit provides diagnosis support information including a pseudo diagnosis result of the abnormality to be diagnosed for the target subject that is derived by the image processing model.

10. The system according to claim 1,
wherein the actual second type image data is actual substance image data including distribution information that visualizes a distribution of a first substance related to an abnormality to be diagnosed,
and the information providing unit provides diagnosis support information including a pseudo index value obtained from pseudo distribution information that corresponds to the distribution of the first substance and is included in the pseudo second type image data of the evaluation target region generated from the individual actual first type image data of the target subject.

11. The system according to claim 1,
wherein the acquisition unit is configured to further acquire attribute information including information relating to biomarkers of the target subject,
the training data includes attribute information including information relating to biomarkers for the plurality of test subjects, and
the information providing unit provides diagnosis support information based on the pseudo second type image data of the evaluation target region that is generated by the image processing model based on the individual actual first type image data of the target subject and on the attribute information of the target subject.

12. The system according to claim 1, further comprising:
an interface capable of accessing a storage that stores the training data; and
a learning unit that trains the image processing model to generate the pseudo second type image data of the evaluation target region from the actual first type image data of the reference region based on the training data.

13. A program including instructions that cause a computer to function as the system according to claim 1.

14. An apparatus that provides the image processing model according to claim 1, comprising:
an interface capable of accessing a storage that stores the training data; and
a learning unit that trains the image processing model so as to generate the pseudo second type image data of the evaluation target region from the actual first type image data of the reference region based on the training data.

15. A method executed by a computer equipped with an interface for acquiring a set of individual actual first type image data including at least a reference region, which includes an evaluation target region as a part, of a target subject, the method comprising:
acquiring a set of individual actual first type image data; and
providing diagnosis support information based on a set of pseudo second type image data of the evaluation target region generated from the set of individual actual first type image data of the target subject by an image processing model machine learned with training data that includes sets of actual first type image data of the reference region of a plurality of test subjects and sets of actual second type image data including the evaluation target region of the plurality of test subjects to generate a set of pseudo second type image data limited to the evaluation target region from a set of actual first type image data of the reference region.

16. The method according to claim 15,
wherein the image processing model is a model including a parameter obtained by learning with a loss function that includes a degree of deviation indicating an extent of deviation of value of image elements in pseudo second type image data of the evaluation target region from value of image elements in actual second type image data of the evaluation target region.

17. The method according to claim 15,
wherein the actual second type image data is actual substance image data including distribution information visualizing a distribution of a first substance related to an abnormality to be diagnosed, and
the image processing model is a model including a parameter obtained by learning, using a loss function including an actual index value obtained from distribution information of the first substance in the evaluation target region of the actual second type image data and a pseudo index value obtained from pseudo distribution information that corresponds to a distribution of the first substance and is included in the pseudo second type image data of the evaluation target region, so that a difference between the actual index value and the pseudo index value is reduced.

18. The method according to claim 17,
wherein the loss function includes a degree of deviation indicating an extent of deviation of values of image elements in the pseudo second type image data of the evaluation target region from values of image elements in the actual second type image data in the evaluation target region.

19. The method according to claim 17,
wherein the evaluation target region includes a plurality of parts, the actual index value is calculated from distribution information of the plurality of parts, and the pseudo index value is calculated from pseudo distribution information of the plurality of parts.

20. The method according to claim 17,
wherein providing the diagnosis support information includes providing diagnosis support information including a pseudo index value obtained from the pseudo second type image data of the evaluation target region generated from the individual actual first type image data of the target subject.

21. The method according to claim 15,
wherein the actual second type image data is actual substance image data including distribution information that visualizes the distribution of a first substance related to an abnormality to be diagnosed,
and providing the diagnosis support information includes providing diagnosis support information including a pseudo index value obtained from pseudo distribution information that corresponds to the distribution of the first substance and is included in the pseudo second type image data of the evaluation target region generated from the individual actual first type image data of the target subject.

22. The method according to claim 15,
wherein the training data includes diagnosis results of the abnormality to be diagnosed for the plurality of test subjects, and
providing the diagnosis support information includes providing diagnosis support information including a pseudo diagnosis result of the abnormality to be diagnosed for the target subject.

23. The method according to claim 15,
wherein the acquiring includes acquiring attribute information including information relating to biomarkers of the target subject,
the training data includes attribute information including information relating to biomarkers for the plurality of test subjects, and
providing the diagnosis support information includes providing diagnosis support information based on the pseudo second type image data of the evaluation target region that is generated based on the individual actual first type image data of the target subject and the attribute information of the target subject.

24. A method executed by a computer including an interface capable of accessing a storage that stores training data including sets of actual first type image data of a reference region, which includes an evaluation target region as a part, of a plurality of test subjects and sets of actual second type image data of the evaluation target region of the plurality of test subjects, the method comprising:

training an image processing model to generate a set of pseudo second type of image data limited to the evaluation target region from a set of actual first type image data of the reference region, based on the training data.

25. The method according to claim 24,
wherein the actual second type image data is actual substance image data including distribution information visualizing a distribution of a first substance related to an abnormality to be diagnosed, and
the training includes learning a parameter of the image processing model, using a loss function including an actual index value obtained from distribution information of the first substance in the evaluation target region of the actual second type image data and a pseudo index value obtained from pseudo distribution information that corresponds to a distribution of the first substance and is included in pseudo second type image data of the evaluation target region, so that a difference between the actual index value and the pseudo index value is reduced.

26. The method according to claim 25,
wherein the loss function includes a degree of deviation indicating an extent of deviation of value of image elements in the pseudo second type image data of the evaluation target region from value of image elements in the actual second type image data of the evaluation target region.

27. The method according to claim 24,
wherein the training data includes attribute information including information relating to biomarkers for the plurality of test subjects, and
the training includes training parameters of the image processing model including the attribute information.

28. The method according to claim 27,
wherein the biomarkers include at least one of information obtained by analyzing blood and information based on genotypes for the plurality of test subjects.

29. The method according to claim 27,
wherein the image processing model includes a convolutional neural network architecture, and
the training includes training parameters of the image processing model so as to include the attribute information in feature values of the convolutional neural network architecture.

30. An image processing model machine learned with training data that include sets of actual first type image data of reference regions, which include evaluation target regions respectively as a part, of a plurality of test subjects and sets of actual second type image data including the evaluation target regions of the plurality of test subjects, so as to generate a set of the pseudo second type image data limited to the evaluation target region from a set of the actual first type image data of the reference region.

* * * * *